(12) United States Patent
Davis et al.

(10) Patent No.: US 10,764,963 B2
(45) Date of Patent: Sep. 1, 2020

(54) VOLATILE MATERIAL DISPENSER

(71) Applicant: S. C. Johnson & Son, Inc., Racine, WI (US)

(72) Inventors: Brian T. Davis, Burlington, WI (US); Kamran Faterioun, New Berlin, WI (US); Kenneth W. Michaels, Spring Grove, IL (US); Stefano Baldessari, Caldonazzo (IT); Alessio Dalser, Vallelaghi (IT); Andrea Pedrotti, Cavedine (IT)

(73) Assignee: S. C. Johnson & Son, Inc., Racine, WI (US)

( * ) Notice: Subject to any disclaimer, the term of this patent is extended or adjusted under 35 U.S.C. 154(b) by 577 days.

(21) Appl. No.: 15/288,892

(22) Filed: Oct. 7, 2016

(65) Prior Publication Data

US 2018/0103507 A1 Apr. 12, 2018

(51) Int. Cl.
| | |
|---|---|
| *H05B 1/02* | (2006.01) |
| *A61L 9/03* | (2006.01) |
| *H05B 3/00* | (2006.01) |

(52) U.S. Cl.
CPC ............ *H05B 1/0244* (2013.01); *A61L 9/032* (2013.01); *A61L 9/037* (2013.01); *H05B 3/0004* (2013.01);
(Continued)

(58) Field of Classification Search
CPC .... A61L 2209/133; A61L 9/032; A61L 9/037; A61L 9/03; H05B 1/0244; H05B 2203/02; H05B 2203/021; H05B 3/0004
(Continued)

(56) References Cited

U.S. PATENT DOCUMENTS 6,862,403 B2 * 3/2005 Pedrotti .............. A01M 1/2072
392/392
6,931,202 B2 * 8/2005 Pedrotti .............. A01M 1/2072
392/392
(Continued)

FOREIGN PATENT DOCUMENTS

CN 202160295 U 0/3201
CN 1832780 A 9/2006
(Continued)

OTHER PUBLICATIONS

International Search Report, Search Strategy, and Written Opinion issued for International Application No. PCT/US2017/053406, dated Mar. 13, 2018, 16 pages.
(Continued)

*Primary Examiner* — Ibrahime A Abraham
*Assistant Examiner* — Frederick F Calvetti
(74) *Attorney, Agent, or Firm* — Quarles & Brady LLP

(57) ABSTRACT

A volatile material dispenser includes a housing configured to receive a refill containing a volatile material and a wick, the housing including a first cavity supporting a heater arrangement and a second, separate cavity supporting a fan arrangement for dispersing a vapor plume of the volatile material. The first cavity is substantially unobstructed between an upper, interior surface of the housing and an upper surface of the heater arrangement. The housing also includes an aperture through which the vapor plume exits the housing and a plurality of openings through which air from the fan arrangement directs the vapor plume away from the aperture. When a refill is received within the hosing, the upper surface of the heater arrangement is disposed nearer the aperture than a distal end of the wick, and a radial gap is formed between the heater arrangement and the wick.

20 Claims, 17 Drawing Sheets

(52) U.S. Cl.
CPC ..... *A61L 2209/133* (2013.01); *H05B 2203/02* (2013.01); *H05B 2203/021* (2013.01)

(58) Field of Classification Search
USPC .................................. 392/386–406, 347–378
See application file for complete search history.

(56) References Cited

U.S. PATENT DOCUMENTS

| | | | |
|---|---|---|---|
| 7,032,831 B2 | 4/2006 | Duston et al. | |
| 7,341,698 B2 * | 3/2008 | Pedrotti | A01M 1/2072 239/34 |
| 7,932,482 B2 * | 4/2011 | Norwood | A01M 1/2077 219/494 |
| 8,320,751 B2 * | 11/2012 | Porchia | A01M 1/2077 392/395 |
| 9,770,524 B2 * | 9/2017 | Belongia | A01M 1/2072 |
| 2003/0138241 A1 * | 7/2003 | Pedrotti | F24F 6/10 392/395 |
| 2005/0195598 A1 * | 9/2005 | Dancs | A61L 9/037 362/231 |
| 2006/0221594 A1 * | 10/2006 | Thuot Rann | A61L 9/037 362/96 |
| 2006/0222347 A1 * | 10/2006 | Wefler | A61L 9/037 392/390 |
| 2006/0237439 A1 * | 10/2006 | Norwood | A61L 9/03 219/506 |
| 2007/0121319 A1 * | 5/2007 | Wolf | A01M 1/2083 362/231 |
| 2009/0162253 A1 * | 6/2009 | Porchia | A61L 9/037 422/124 |
| 2011/0139885 A1 | 6/2011 | Gasper et al. | |
| 2012/0012668 A1 * | 1/2012 | Belongia | A01M 1/2072 239/34 |
| 2014/0037273 A1 | 2/2014 | Jaworski et al. | |
| 2014/0064713 A1 * | 3/2014 | Niemiec | A61L 9/035 392/387 |

FOREIGN PATENT DOCUMENTS

| | | |
|---|---|---|
| CN | 201014704 Y | 1/2008 |
| CN | 101160142 A | 4/2008 |
| CN | 101690385 A | 3/2010 |
| CN | 101801697 A | 8/2010 |
| CN | 101056659 B | 10/2010 |
| CN | 201611958 U | 10/2010 |
| CN | 201637075 U | 11/2010 |
| CN | 101951966 A | 1/2011 |
| CN | 201928457 U | 8/2011 |
| CN | 102333391 B | 1/2012 |
| CN | 202274611 U | 6/2012 |
| CN | 102655773 A | 9/2012 |
| CN | 102685950 A | 9/2012 |
| CN | 202617391 U | 12/2012 |
| CN | 102869129 A | 1/2013 |
| CN | 102970781 A | 3/2013 |
| CN | 202841559 U | 3/2013 |
| CN | 103096939 A | 5/2013 |
| CN | 202957997 U | 5/2013 |
| CN | 103388948 A | 11/2013 |
| CN | 103743088 A | 4/2014 |
| CN | 103743093 A | 4/2014 |
| CN | 103747828 A | 4/2014 |
| CN | 203590481 U | 5/2014 |
| CN | 103933596 A | 7/2014 |
| EP | 1247446 B1 | 10/2002 |
| EP | 1283062 B1 | 5/2006 |
| EP | 1800698 B1 | 1/2009 |
| EP | 1492574 B1 | 7/2009 |
| EP | 2193690 B1 | 6/2010 |
| EP | 2193039 B1 | 10/2010 |
| EP | 1613362 B1 | 12/2010 |
| EP | 2120545 B1 | 9/2011 |
| EP | 2429844 A1 | 3/2012 |
| EP | 1432456 B1 | 12/2012 |
| EP | 2467017 B1 | 5/2013 |
| EP | 2240209 B1 | 7/2013 |
| EP | 2657708 A1 | 10/2013 |
| EP | 2593146 B1 | 6/2014 |
| WO | 9846283 A1 | 10/1998 |
| WO | 2003028775 A1 | 4/2003 |
| WO | 2004031675 A1 | 4/2004 |
| WO | 2005092400 A1 | 10/2005 |
| WO | 2006105154 A2 | 10/2006 |
| WO | 2007035201 A2 | 3/2007 |
| WO | 2009060212 A2 | 5/2009 |
| WO | 2010014950 A1 | 2/2010 |
| WO | 2010132565 A1 | 11/2010 |
| WO | 2011020480 A1 | 2/2011 |
| WO | 2011159802 A1 | 12/2011 |
| WO | 2012011295 A1 | 1/2012 |
| WO | 2013025921 A1 | 2/2013 |
| WO | 2014022164 A2 | 2/2014 |
| WO | 2014037259 A1 | 3/2014 |
| WO | 2014040988 A2 | 3/2014 |
| WO | 2014055478 A2 | 4/2014 |

OTHER PUBLICATIONS

Grounds for Rejection issued in Chinese Patent Application No. 201780061825.6, May 21, 2020, 13 pages.

* cited by examiner

VOLATILE MATERIAL DISPENSER

BACKGROUND OF THE DISCLOSURE

1. Field of the Disclosure

The present disclosure relates generally to volatile material dispensers for volatilizing volatile materials and, more particularly, to volatile material dispensers having a heater and fan for volatilization of a volatile material.

2. Description of the Background of the Disclosure

Various volatile material dispensers are known in the prior art and generally include a housing with a refill inserted therein. The refill generally includes a container for holding a volatile material therein. In some dispensers, the volatile material is passively emitted therefrom. In other dispensers, a diffusion element is utilized to facilitate the dispensing of the volatile material. Examples of diffusion elements include heaters such as positive temperature coefficient (PTC) heaters, piezoelectric elements, fans, aerosol actuators, and the like. Regardless of the manner in which the volatile material is emitted, once the volatile material has been expended from the refill, the refill is removed by a user and replaced with a new refill.

One type of volatile material dispenser, which is sometimes referred to as a plug-in scented oil dispenser, includes a housing and a heater disposed within the housing. A refill for use with a plug-in scented oil dispenser generally includes a container with a volatile material therein and a wick in contact with the volatile material and extending out of the refill. Upon insertion of the refill into the dispenser, at least a portion of the wick is disposed adjacent the heater such that volatile material that moves through the wick is volatilized by the heater. The volatile material dispenser typically includes a plug assembly having electrical prongs extending outwardly from the housing. The electrical prongs are inserted into a standard electrical outlet and thereafter supply electrical energy to the volatile material dispenser. One such dispenser is disclosed in the commonly-assigned U.S. Patent Publication 2014/0037273. Plug-in scented oil dispensers may also utilize a fan to aid in vaporizing and dispersing volatile material.

SUMMARY OF THE INVENTION

According to a first aspect, a volatile material dispenser includes a housing configured to receive a refill containing a volatile material and a wick, the housing including a first cavity supporting a heater arrangement and a second, separate cavity supporting a fan arrangement for dispersing a vapor plume of the volatile material. A chimney is provided between an upper, interior surface of the housing and an upper surface of the heater arrangement. The housing also includes an aperture through which the vapor plume exits the housing and a plurality of openings through which air from the fan arrangement is directed away from the aperture and toward the vapor plume. When the refill is received within the housing, the upper surface of the heater arrangement is disposed nearer the aperture than a distal end of the wick, and a radial gap is formed between the heater arrangement and the wick.

According to another aspect, a volatile material dispenser includes a housing configured to receive a refill containing a volatile material and a wick. The housing supports a heater arrangement to volatize the volatile material into a vapor plume and further supports a fan arrangement for dispersing the vapor plume. The housing includes an aperture extending along a first axis and through which a vapor plume of the volatized material exits the housing. The housing further includes a plurality of openings through which air from the fan arrangement is directed away from the aperture. The housing additionally defines a solid panel adjacent to and spaced rearward from the aperture, the solid panel formed in a gap between two of the plurality of openings and having a width substantially equal to a width of the aperture. At least one of the fan arrangement and the plurality of openings is angled along a second axis, the second axis being angled upward relative to a line perpendicular to the first axis.

According to yet another aspect, a volatile material dispenser includes a housing configured to receive a refill containing a volatile material and a wick. The housing supports a heater arrangement to volatize the volatile material into a vapor plume and a fan arrangement for dispersing the vapor plume. The housing includes a concave upper surface defining an aperture through which a vapor plume of the volatized material exits the housing and a plurality of openings through which air from the fan arrangement is directed away from the aperture. The concave upper surface includes a leading edge angled rearwardly from a front of the housing to a top of the housing, such that the plurality of openings are deepest proximate the aperture and get progressively shallower toward the top of the housing. Additionally, the aperture is elevated relative to a portion of the concave upper surface disposed between the aperture and a front of the housing, the portion of the concave upper surface angling downwardly between the aperture and the front of the housing.

DETAILED DESCRIPTION

Figure 1:
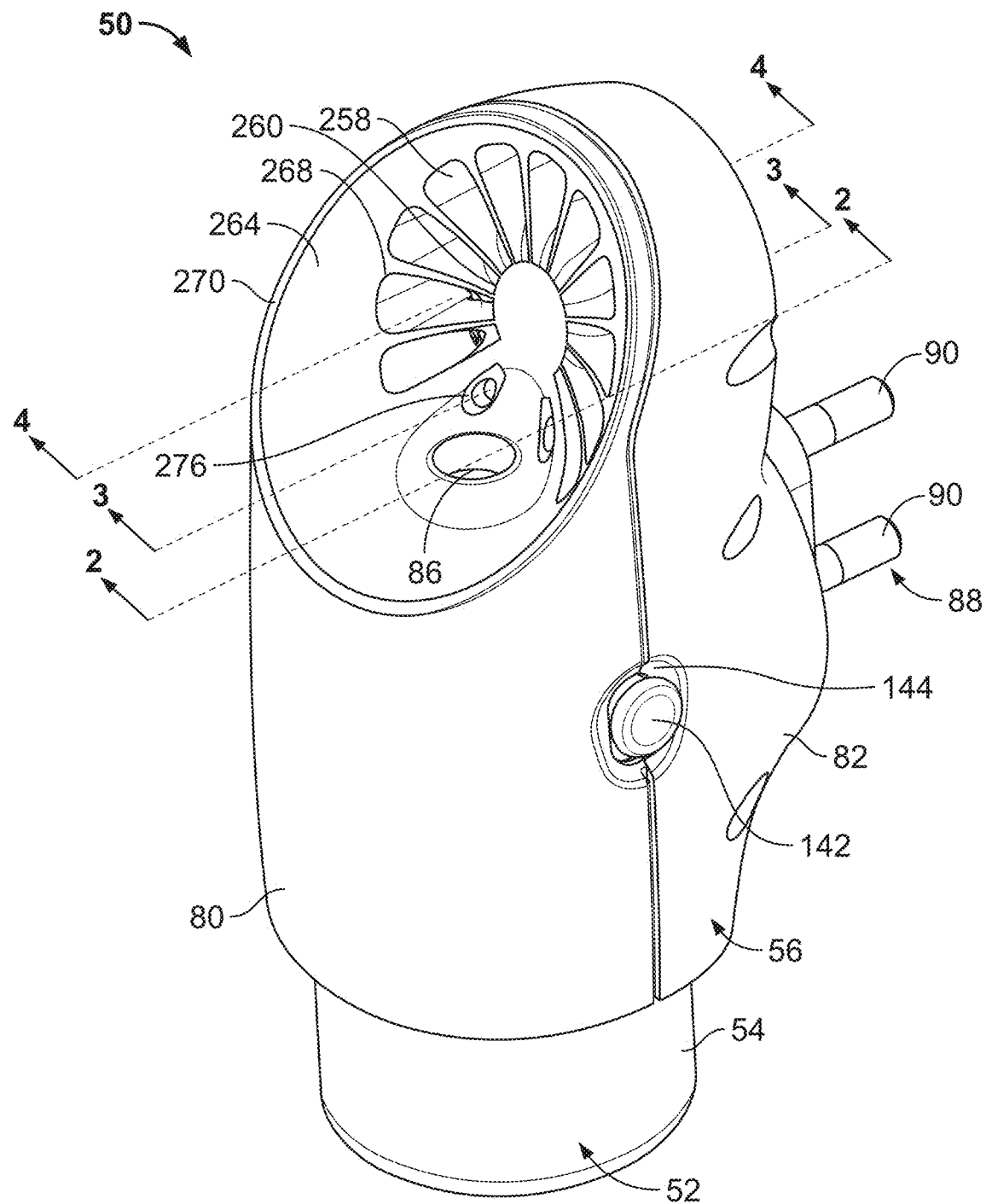
FIG. 1 is a top isometric view of a first embodiment of a dispensing system including a dispensing device and a refill for use therewith.

The present disclosure is directed to heater and fan arrangements for volatile material dispensers that reduce condensation of the volatile material back onto the dispensers after that volatile material is emitted from the dispensers. While the present disclosure may be embodied in many different forms, the present disclosure is to be considered only as an exemplification of the principles of the disclosure, and it is not intended to limit the disclosure to the embodiments illustrated.

Referring to the drawings, FIGS. 1-9 depict a volatile material dispenser 50 adapted to accommodate a refill 52. The refill 52 includes a container 54 with a volatile material therein, wherein the container 54 is adapted to be retained by a housing 56 of the dispenser 50. The container 54 includes a retaining mechanism 58 (see FIG. 2) to hold a wick 60 within the container 54 and a body 62 with the volatile material disposed therein. The body 62 includes a base portion 64 and a sidewall 66 that extends upwardly toward a top wall 68. In one instance, the sidewall may be generally cylindrical, although other sidewall configurations are possible. The top wall 68 also may be integral with a neck 70.

The neck 70 of the refill 52 includes a threaded portion disposed on an outer surface thereof and an opening 72 disposed through a top portion thereof, wherein the opening 72 allows access to the volatile material. The retaining mechanism 58 is disposed within the neck 70 and further includes a sheath 76 that extends around at least a portion of the wick 60 to protect the wick 60. In the present embodiment, an upper, free end 78 of the wick 60 extends above the sheath 76. Although a specific dispenser 50 and container 54 are described with particularity, it is contemplated that the heater and fan arrangements disclosed herein may be utilized in conjunction with any type of refill and/or container. For example, useful containers include, but are not limited to, the containers described in U.S. Pat. No. 7,032,831, and the containers described in U.S. Pat. Pub. 2011/0139885, both of which are owned by the same assignee as the present disclosure.

The volatile material disposed in the container 54 may be any type of volatile material adapted to be dispensed into an environment. For example, the container 52 may include a cleaner, an insecticide, an insect repellant, an insect attractant, a disinfectant, a mold or mildew inhibitor, a fragrance, a disinfectant, an air purifier, an aromatherapy scent, an antiseptic, an odor eliminator, a positive fragrancing volatile material, an air-freshener, a deodorizer, or the like, and combinations thereof. Additives may be included in the volatile material, such as, for example, fragrances and/or preservatives.

Now turning generally to FIGS. 1-4, the housing 56 of the volatile material dispenser 50 generally includes front and rear portions 80, 82 attached to one another to form a first interior chamber or cavity 84 therebetween. The front portion 80 also defines an aperture 86 at a top of the housing 56 for the emission of volatile material therethrough. In another aspect, the aperture 86 may be defined at an intersection of the front and rear portions 80, 82. The refill 52 is inserted into the housing 56 by inserting the wick 60 upwardly into the first chamber 84, such that the wick extends along a direction defined by an axis, $a_w$, the axis preferably being substantially vertical when the dispenser 50 is in use. The aperture 86 may be disposed directly above the wick 60 and also may be centered on the axis, $a_w$.

Figure 2:
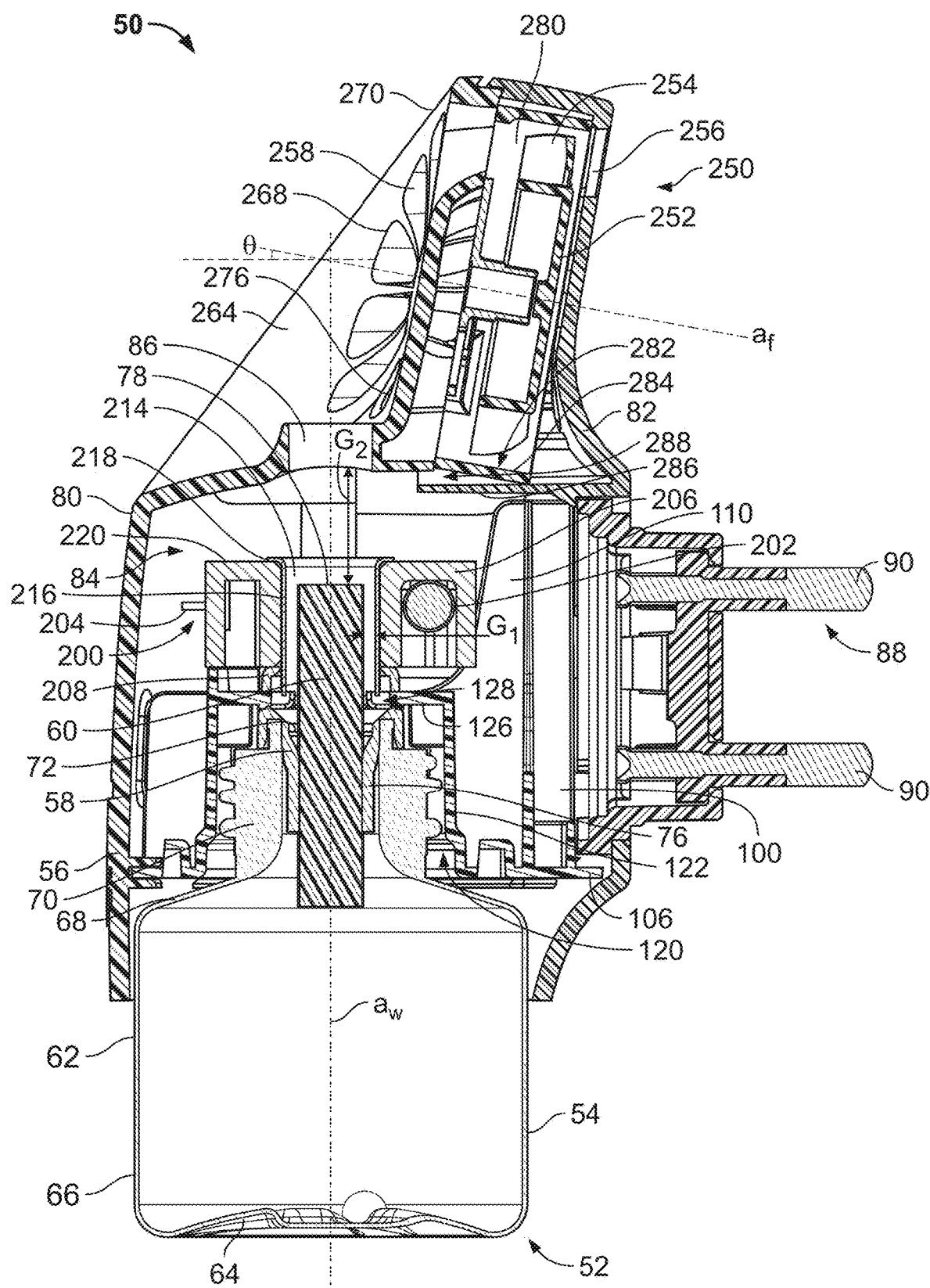
FIG. 2 is a cross-sectional view of the dispensing system of FIG. 1 taken generally along the line 2-2 of FIG. 1.
Figure 5:
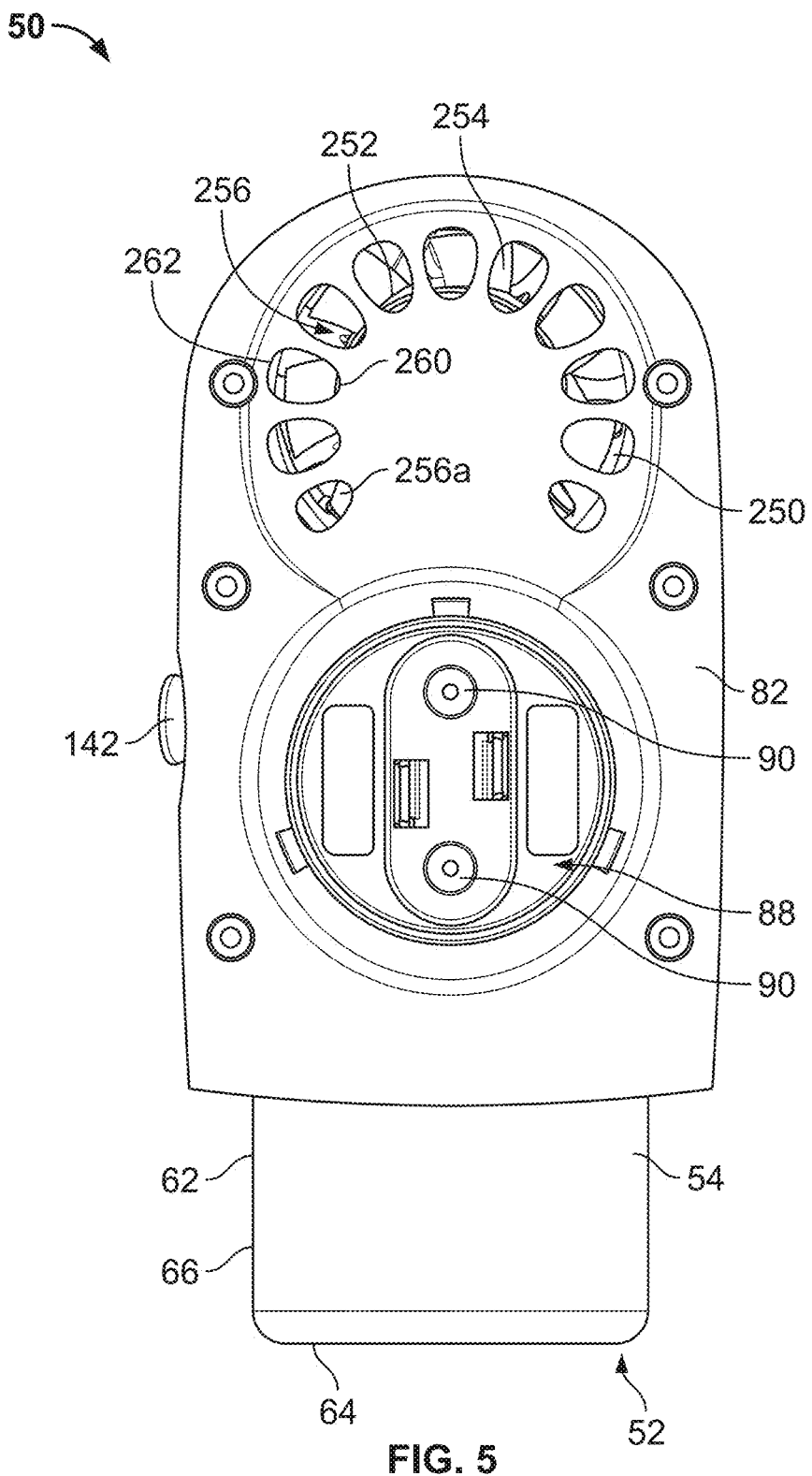
FIG. 5 is a rear view of the dispensing system of FIG. 1.

Referring to FIGS. 1, 2, and 5, a plug assembly 88 extends from the rear portion 82 of the housing 56 and includes a plurality of electrical prongs 90 adapted for insertion into a conventional outlet. The plug assembly may be varied from the one shown by being adapted for use in any other country. In addition, the plug assembly 88 may include any features known in the art, for example, the plug assembly 88 may be partially or fully rotatable.

As best seen in FIGS. 2, 3, and 6-8, a stationary support 100 is disposed within the housing 56 and extends laterally within the first chamber 84, at least partially between first and second sides 102, 104 of the housing 56. The support 100 includes a generally planar wall 106 and first and second arms 108, 110 extending upwardly from the planar wall 106 between the front and rear portions 80, 82 of the housing. In one aspect, the arms 108, 110 may extend substantially between the front and rear portions 80, 82 of the housing.

Figure 3:
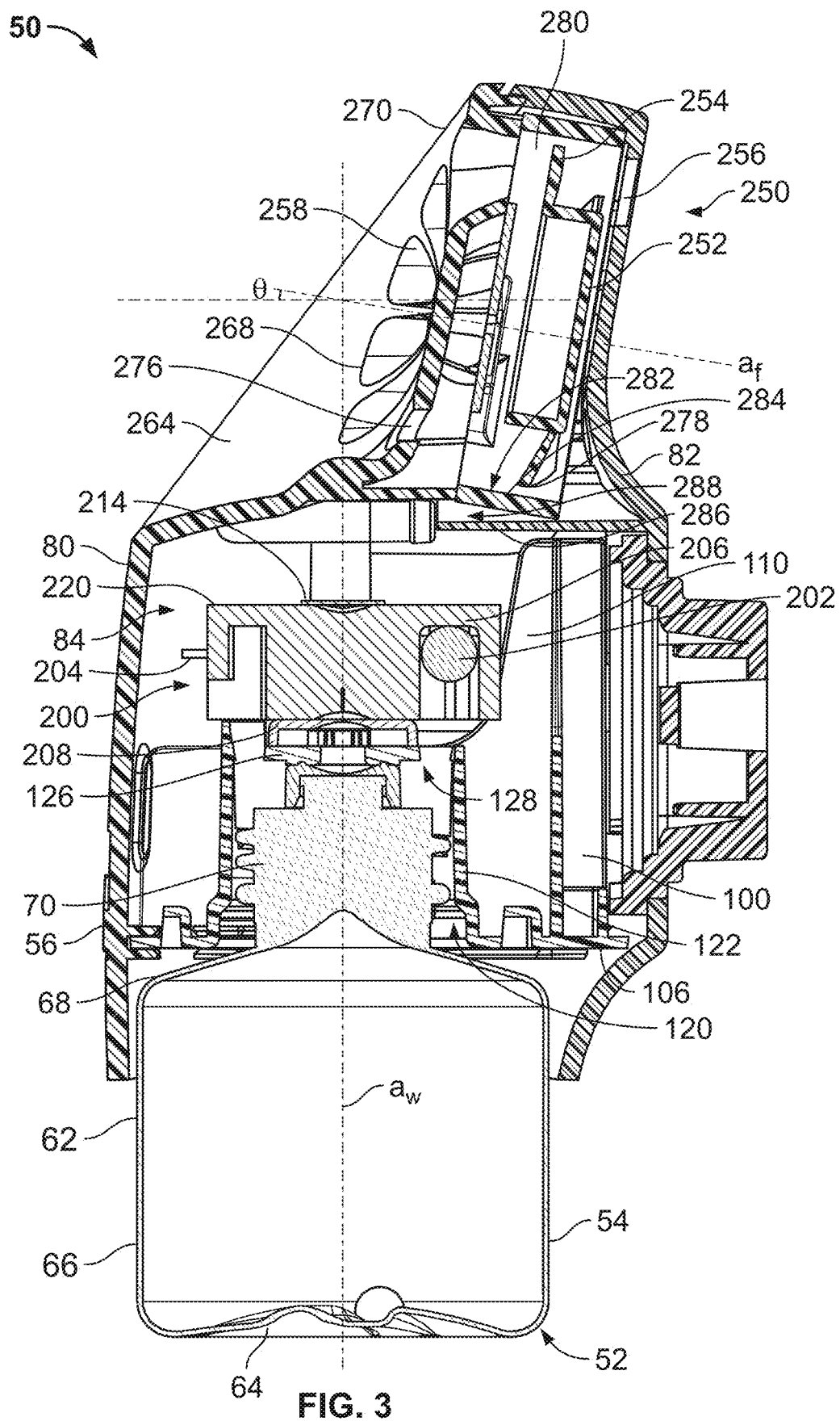
FIG. 3 is a cross-sectional view of the dispensing system taken generally along the line 3-3 of FIG. 1.
Figure 8:
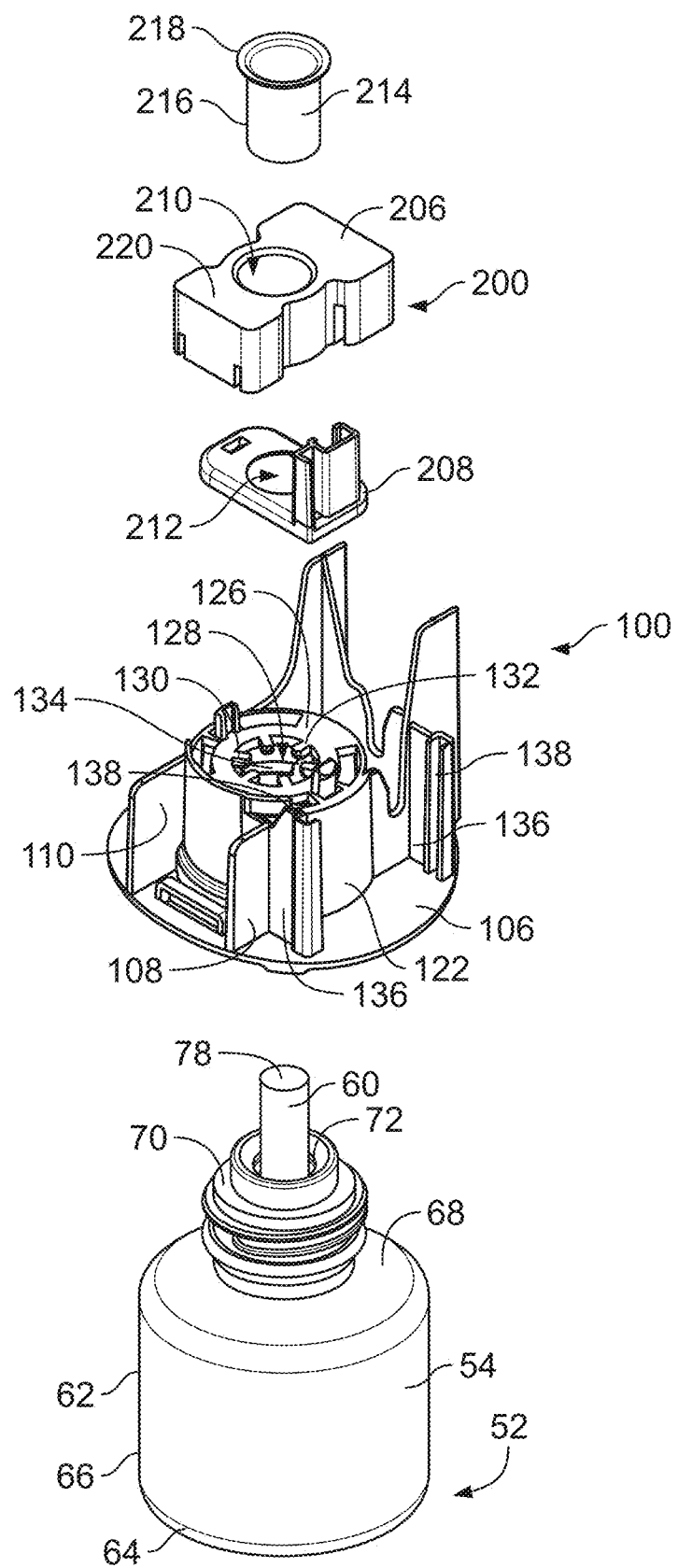
FIG. 8 is an exploded view of a refill and portions of the dispenser of FIG. 1.

The planar wall 106 of the support 100 includes an aperture 120 therethrough, as seen in FIGS. 2 and 3, and it will be understood that the aperture 120 may be cylindrical, given the shape of the neck 70 of the refill 52. A cylindrical member 122 extends upward from a periphery of the circular aperture 120. The cylindrical member 122 is partially enclosed by a cover 126 with an aperture 128 for the wick 60. The aperture 128 may include one or more wick centering mechanisms 130, such as one or more tabs 132 extending inward from the periphery of the aperture 128, as seen in FIG. 8. In one aspect, there may be an even number of tabs, and each tab may have a diametrically-opposed counterpart. Additionally, FIG. 8 also illustrates that an interior portion of the cylindrical member 122 may include a retaining mechanism 134 such as threading or one or more inwardly extending members, in order to releasably couple with the retaining mechanism 58 of the container 54.

Figure 6:
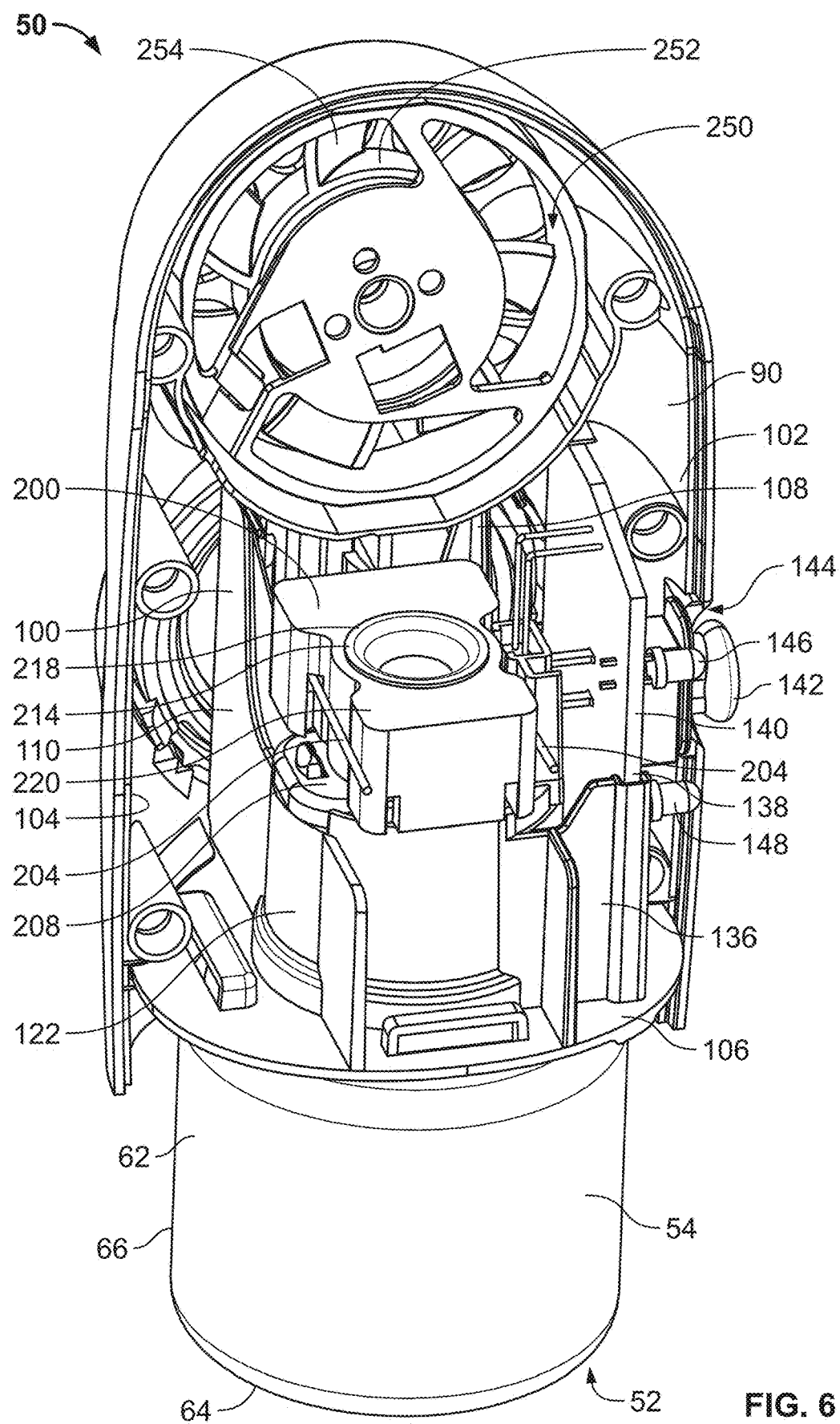
FIG. 6 is a front and top isometric view of the dispensing system of FIG. 1 with a front portion of the housing removed to detail internal components of the dispensing system.
Figure 7:
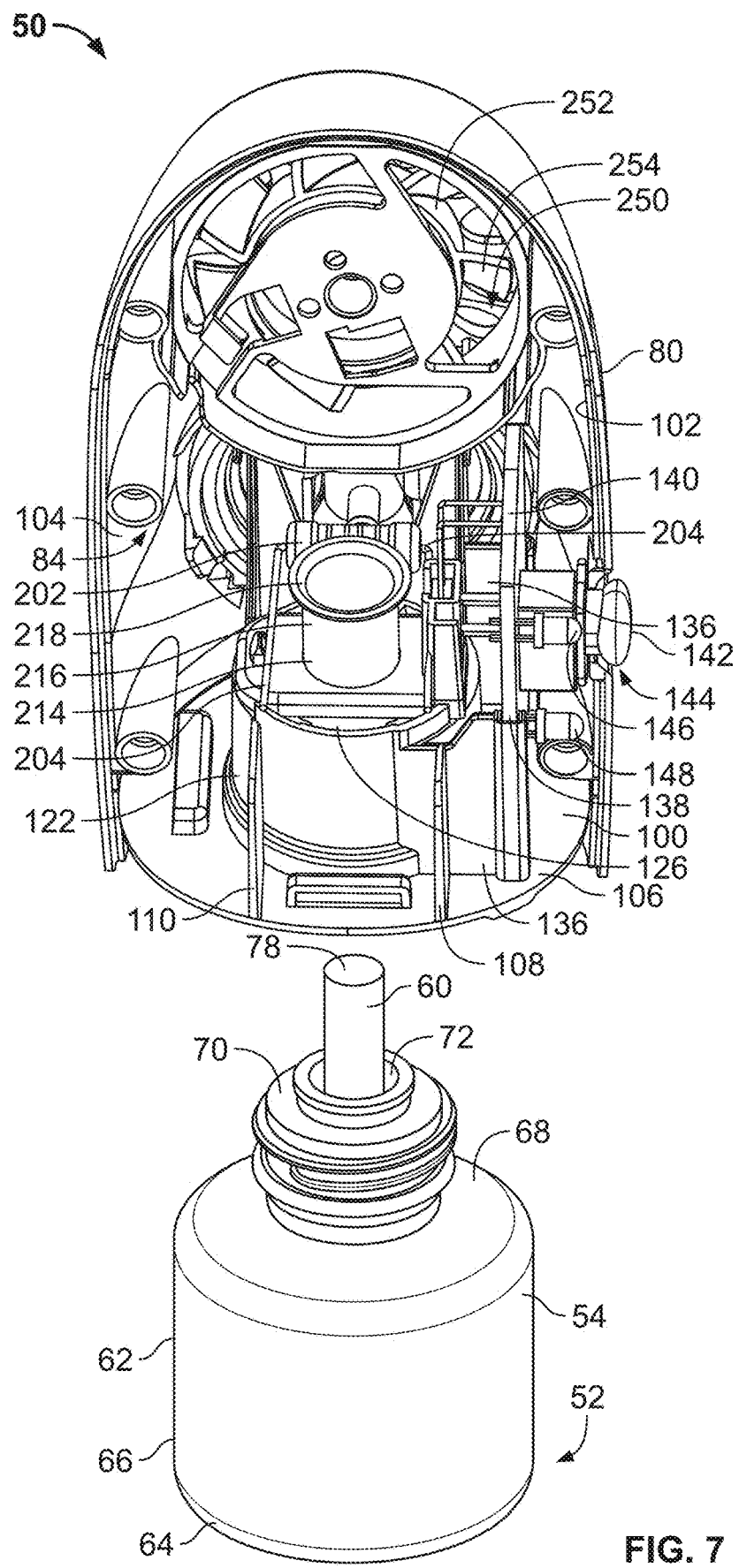
FIG. 7 is a front and top isometric view of the dispensing system of FIG. 1, with both the front portion of the housing and portions of the heater arrangement removed for clarity.

The support 100 also includes a plurality of arms 136 extending outward from the first arm 108, the arms 136 each defining a channel 138 configured to receive an edge of a circuit board 140, as best seen in FIGS. 6 and 7. The circuit board 140 is electrically coupled to a button 142, a switch, a slider, or any other component that is configured to turn the dispenser 50 on and off. The button 142 may be disposed within an opening 144 defined by one or more of the front portion 80 and rear portion 82 of the housing 56. The same component, or another component, also may be electrically coupled to the circuit board and may be configured to vary the power level of the dispenser 50, e.g., between "Off," "Low," and "High" settings.

Additionally, one or more light emitting diodes (LEDs) 146, 148 may be electrically coupled to the circuit board 140 in order to indicate a status of the dispenser 50. For example, a first LED 146 may illuminate a first color when the dispenser 50 is in a "Low" setting, and a second LED 148 may illuminate a second color when the dispenser 50 is in a "High" setting. The second LED 148 may illuminate by itself in the high setting, or the lighting may be additive, such that both that first LED 146 and the second LED 148 illuminate in the high setting. Alternatively, the first LED 146 may be illuminated when the dispenser 50 is plugged in but not on, and the second LED 148 may be illuminated when the dispenser 50 is plugged in and turned on. The dispenser 50 may include one or more separate openings in the housing 56 or translucent portions of the housing 56 to permit passage of a portion of each LED or of the light emitted by each LED. Alternatively, light from one or both LEDs may be visible through the opening 144, e.g., if there is a gap between a sidewall of the opening 144 and the button 142 or if at least a portion of the button 142 is translucent.

While the dispenser is disclosed as having particular switches, one skilled in the art will appreciate the dispenser may include any number of switches and/or may include any suitable types of switches, for example, timing switches, on/off switches, setting switches, switches controlling the fan, switches controlling the heater, and/or any other suitable switches.

Referring again to FIGS. 2, 3, and 6-8, the dispenser 50 further includes a heater arrangement 200 employing a heater or resistor(s) 202 electrically coupled via a plurality of connectors 204 to the circuit board 140. The resistor 202 may be potted, embedded, or otherwise disposed within a housing 206, the housing 206 disposed proximate the cover 126 of the stationary support 100. As those figures illustrate, a bracket 208 may be integral with or couple on an underside to the cover 126 and may abut or couple to the housing 206 at a topside. Each of the housing 206 and bracket 208 may define an opening 210, 212, respectively, that are coaxial with the aperture 128 and that, like the aperture 128, are configured to receive the wick 60. Additionally, the heater arrangement 200 may include a conducting member 214 defining a generally cylindrical body 216 that terminates at an upper end in a radially expanding flange 218. The cylindrical body 216 has an inner diameter sized to receive the wick 60 and an outer diameter configured to retain the housing 206 in position. Specifically, as seen in FIG. 2, the outer diameter of the cylindrical body 216 may be such as to press fit within the openings 212 and/or 210. Moreover, when inserted fully, the flange 218 of the conducting member 214 may abut an upper surface 220 of the housing 206, thereby preventing vertical displacement of the housing 206 and resistor 202 relative to the rest of the heater arrangement 200. Heat from the resistor 202 heats the housing 206, which transfers heat to the conducting member 214. The conducting member 214 may be made of a metallic or other conductive material, so that heat quickly moves through the conducting member 214, creating a uniform ring of heat to evenly apply heat to the wick 60 about an outer surface of the wick 60.

The housing 206 and/or any potting disposed within the housing 206 may comprise a ceramic, aluminum, or other thermally conductive material, such that the housing 206 is configured to convert the localized heating of the resistor 202 to a radiant heat source surrounding the wick 60 on a plurality of sides. Additionally, as best seen in FIG. 2, the heater arrangement 200, generally, and the resistor 202 in particular are longitudinally disposed proximate the upper, free end 78 of the wick 60, which may lead to optimal evaporation of the fluid drawn from the container 54 by the wick 60. In one aspect, also as seen in FIG. 2, the heater arrangement 200 may extend longitudinally above the upper, free end 78 of the wick 60, in order to continue heating volatilized material, even after the material has dispersed from the wick 60. This configuration also may permit the heater to be disposed closer to the aperture 86, again retaining the volatilized material at an elevated temperature for a longer period of time, thereby decreasing condensation of the material.

As seen in FIGS. 2 and 3, the resistor 202 within the heater arrangement 200 may be disposed rearward of the wick 60, i.e., between the wick 60 and the plug assembly 88. This configuration may permit a front portion of the heater arrangement 200 to be narrower, which may permit the wick 60, and, consequently, the aperture 86, to be disposed laterally closer to a front side of the housing 56. As a result, the dispenser 50 may include less material forward of the aperture 86 onto which the volatilized material can condense. Similar results also may be achieved by locating the resistor 202 on either lateral side of the wick 60, i.e., at a location other than between the wick 60 and the forward wall, although that configuration also may be possible.

In one aspect, the heater arrangement 200 may be a positive temperature coefficient (PTC)-type heater or thermistor, either potted or assembled without potting. Alternatively, the heater arrangement 200 may include a ceramic cylinder coated in a resistive metal oxide, a carbon film, or a resistive film and wrapped with a resistive wire or flexible heating element. Other types of heater arrangements 200 may be employed, as would be appreciated by one of ordinary skill in the relevant art.

Figure 10:
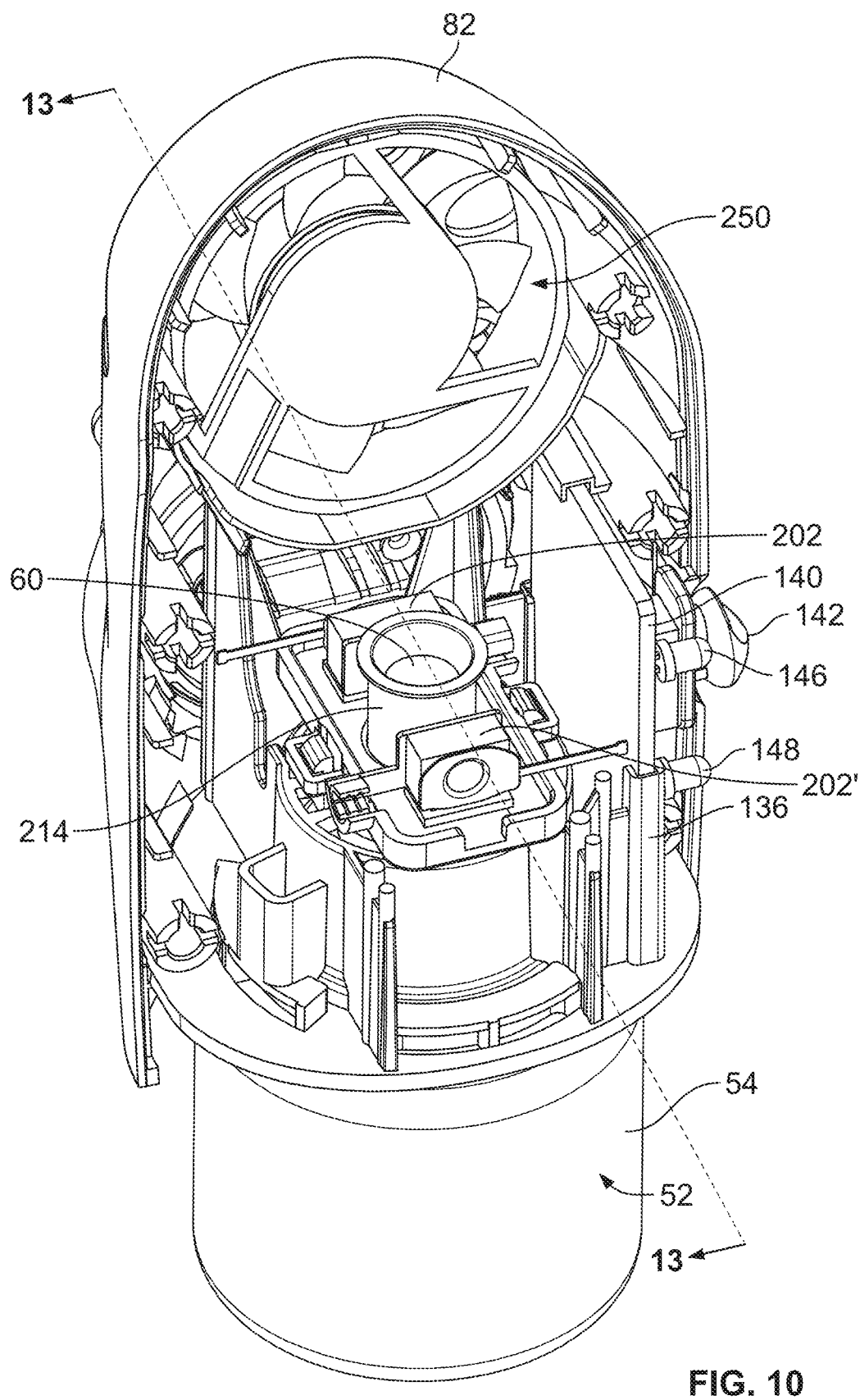
FIG. 10 is a front and top isometric view of another aspect of a dispensing system with a front portion of the housing removed to detail internal components of the dispensing system and a plurality of heaters surrounding the wick.

In another aspect, as seen in FIG. 10, a plurality of resistors or PTC thermistors may be disposed within the first cavity 84. Specifically, a first heater or resistor 202 may be disposed rearward of the conducting member 214, and a second heater or resistor 202' may be disposed forward of the conducting member 214, e.g., diametrically opposed from the first heater or resistor 202. In still further illustrative embodiments, a plurality of resistors or PTC thermistors may be arranged in a tubular arrangement or within a tubular structure surrounding the wick 60 to form a tubular heater arrangement. In still alternative illustrative embodiments, two or more of the heater arrangements may be stacked in a vertical fashion, with the wick 60 inserted through or alongside the two or more heater arrangements. When multiple heaters 202 are used, each heater may be of the same type, e.g., all resistors or all PTC elements. Alternatively, the dispenser 50 may incorporate heaters of multiple types, e.g., one resistor and one PTC element, in any order or arrangement. In this manner, one or more of the heaters, which may be operated independently, may be operated at any point in time. In an illustrative embodiment, a first heater having a first resistance may be actuated for a low level of heat, a second heater having a second resistance or temperature greater than the first resistance or temperature may be actuated for a medium level of heat, and both heaters may be actuated for a high level of heat. Optionally, multiple resistors may be formed on a single ceramic tube to create the same effect. In another illustrative embodiment, a first heater may be actuated for a NORMAL mode, in which the fan (described in greater detail below) is not on, and a second heater, by itself or in combination with the first heater, as well as with the fan, may be actuated in a BOOST mode. It should be understood that any combination of heaters, resistance levels, and/or levels of heat are within the scope of the present application.

Although the heater arrangements herein are described as being utilized with dispensers that utilize liquid electric refills, the heater arrangements may be utilized for any electrical dispenser from which any type of volatile material is dispensed out of any type of refill by way of a heater, e.g., scented oils, insect repellant, etc. Optionally, a dispenser employing any of the heater arrangements disclosed herein may further include one or more heaters and/or additional devices for dispensing the volatile material, for example, one or more of a fan (as discussed below), a piezoelectric element, and/or other components disposed in a housing thereof to help facilitate the release of volatile material.

Referring to FIG. 2, a gap, $G_1$, may be defined by a volume extending radially outward from a distal end of the wick 60 to one or more surfaces within the dispenser 50, e.g., between an outer periphery or outer diameter of the wick 60 and an inner periphery or inner diameter of the conducting member 214 or the housing 206 that may hold the heater 202. The gap, $G_1$, should be large enough to allow sufficient airflow through the heater arrangement 200 or the heater 202, but small enough to provide sufficient heat transfer to the wick 60. In illustrative embodiments, the gap may be substantially constant, both radially about the axis, $a_w$, and longitudinally along that axis, in the region at which the wick 60 and the heater 202 or the conducting member 214 overlap. The gap, $G_1$, may be between about 0.5 millimeter and 2.5 millimeters. In alternative illustrative embodiments, the gap is between about 1.0 millimeter and about 2.0 millimeters. In yet other illustrative embodiments, the gap is about 1.0 millimeter or about 1.5 millimeters. In another aspect, the gap may be non-uniform, and the values above may represent maximum, minimum, or average radial clearance amounts.

In another aspect, the gap, $G_1$, may be defined in terms of an average cross-sectional area along the distal end of the wick 60, e.g., between about 10 mm$^2$ and about 30 mm$^2$ at each cross-section along a length of the distal portion. In yet another aspect, the gap, $G_1$, may be defined in terms of an average volume, e.g., between about 50 mm$^3$ and about 250 mm$^3$ in one example, and between about 100 mm$^3$ and about 200 mm$^3$ in another example.

Heat from the heater arrangement 200 travels inwardly through the air gap $G_1$ toward the wick 60 through conduction and radiation and gets trapped around the wick 60, thereby increasing the overall temperature in the gap $G_1$ and therefore in the wick 60, creating a distribution of heat around a circumference of the wick 60, and further increasing volatilization of the volatile material in the wick 60. In one aspect, heat may be distributed substantially uniformly about a circumference of the wick. Additionally, or alternatively, heat may be distributed substantially uniformly longitudinally along the wick 60 and/or the heater 202. In still another aspect, the heater 202 may apply a greater or lesser amount of heat at different longitudinal or radial portions of the wick 60, e.g., by locating the heater closer to or farther from the wick, by forming the housing 206 of more or less thermally conductive material at different longitudinal or radial positions, by adding one or more additional heaters at different locations, or by modifying the geometry of the housing 206 to be closer to or farther from the wick 60 at different locations.

Figure 13:
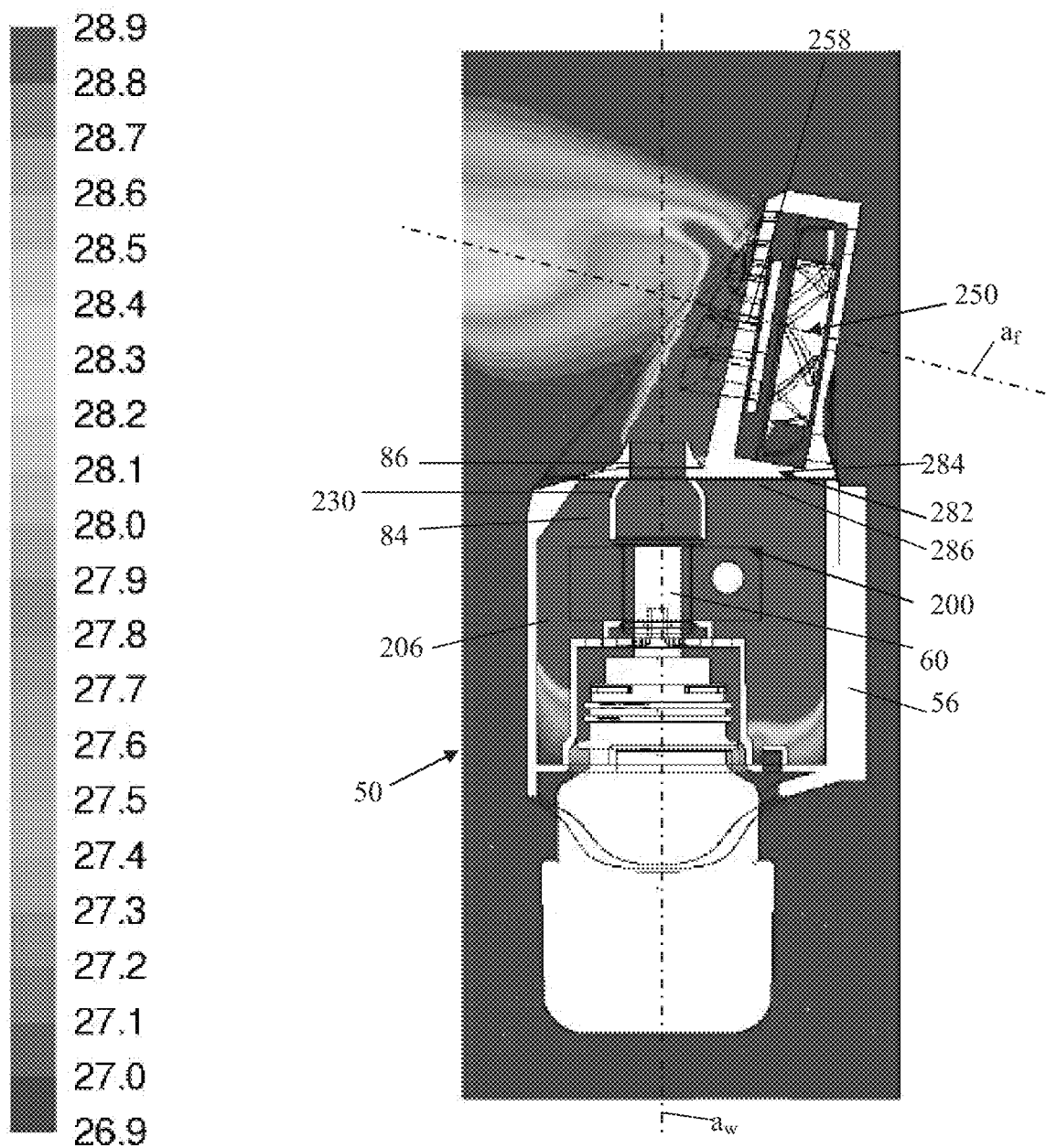
FIG. 13 is a gas temperature plot of the dispensing system of FIGS. 10 and 11 taken generally along the line 13-13 of FIG. 10.

The heater arrangement 200 also may be substantially exposed to the open space within the first chamber 84, as best seen in FIGS. 2, 3, and 6. Thus, as seen in FIG. 13, in addition to heating the wick 60 in order to volatilize material, the heater arrangement 200 may radiate heat through the exterior walls of the housing 206, particularly through the exterior side walls and the top wall, to elevate the temperature within the first chamber 84. At elevated temperatures, volatilized material within the first chamber 84 may be more likely to remain volatilized, providing more time for the dispenser to evacuate that material through the aperture 86 to be dispersed into the environment rather than condensing within the first chamber 84. Accordingly, referring again to FIGS. 2, 3, and 6, the dispenser 50 may remain substantially unobstructed between an upper, interior surface of the front portion 80 and an upper surface of the housing 206 of the heater arrangement 200.

A second gap $G_2$ also may be disposed between an upper end of the wick 60 or an upper end of the flange 218 or the upper surface 220 of the housing 206 and a lower extent of the aperture 86 in the housing 56, which may be longitudinally and/or laterally aligned with the wick 60 when the refill 52 is inserted into the housing 56. The gap $G_2$ should be large enough to form a warm air pocket that promotes evaporation or volatilization and an upward draft of the vapor emanating from the wick 60, but small enough to prevent condensation of the evaporated fluid within the cavity 84 or soon after exiting the aperture 94. In illustrative embodiments, the gap measures between about 5 millimeters and 15 millimeters in an axial direction. In alternative illustrative embodiments, the gap is between about 7 millimeters and about 12 millimeters axially. In yet other illustrative embodiments, the gap is about 10 millimeters axially.

In another aspect, the gap may be defined in terms of a volume disposed between an uppermost area of the wick 60 and a lowermost area of the aperture 86. The volume may be defined by an imaginary line forming a perimeter, the imaginary line surrounding a periphery of either the wick or the wick plus the first gap, $G_1$, and then extending upward to the aperture. Alternatively, the imaginary line may surround a periphery of the aperture and then extend downward to the wick. The periphery of the aperture and the periphery of the wick, or of the wick plus the first gap, may be approximately the same radial distance away from the axis, $a_w$, such that the volume may be generally cylindrical. Alternatively, the periphery of one section may be larger or smaller than the periphery of the other section, such that the imaginary line defining the volume may taper or expand along the length of the volume.

The volume may define an unobstructed chimney through which a majority of the volatilized material may be drawn, e.g., upward, from the area around the wick to an exterior of the housing 56. In this regard, the fan arrangement 250 (described below in greater detail) may serve a plurality of purposes. In addition to dispersing the volatilized material into the environment once it has left the interior chamber, it also may create a reduced air pressure zone in or around the aperture 86, external to the dispenser 50. That negative relative air pressure may serve to draw the volatilized material outward from within the housing for dispersal to the environment, while at the same time reducing the amount of volatile material dispersed within the remainder of the interior chamber 84.

Figure 11:
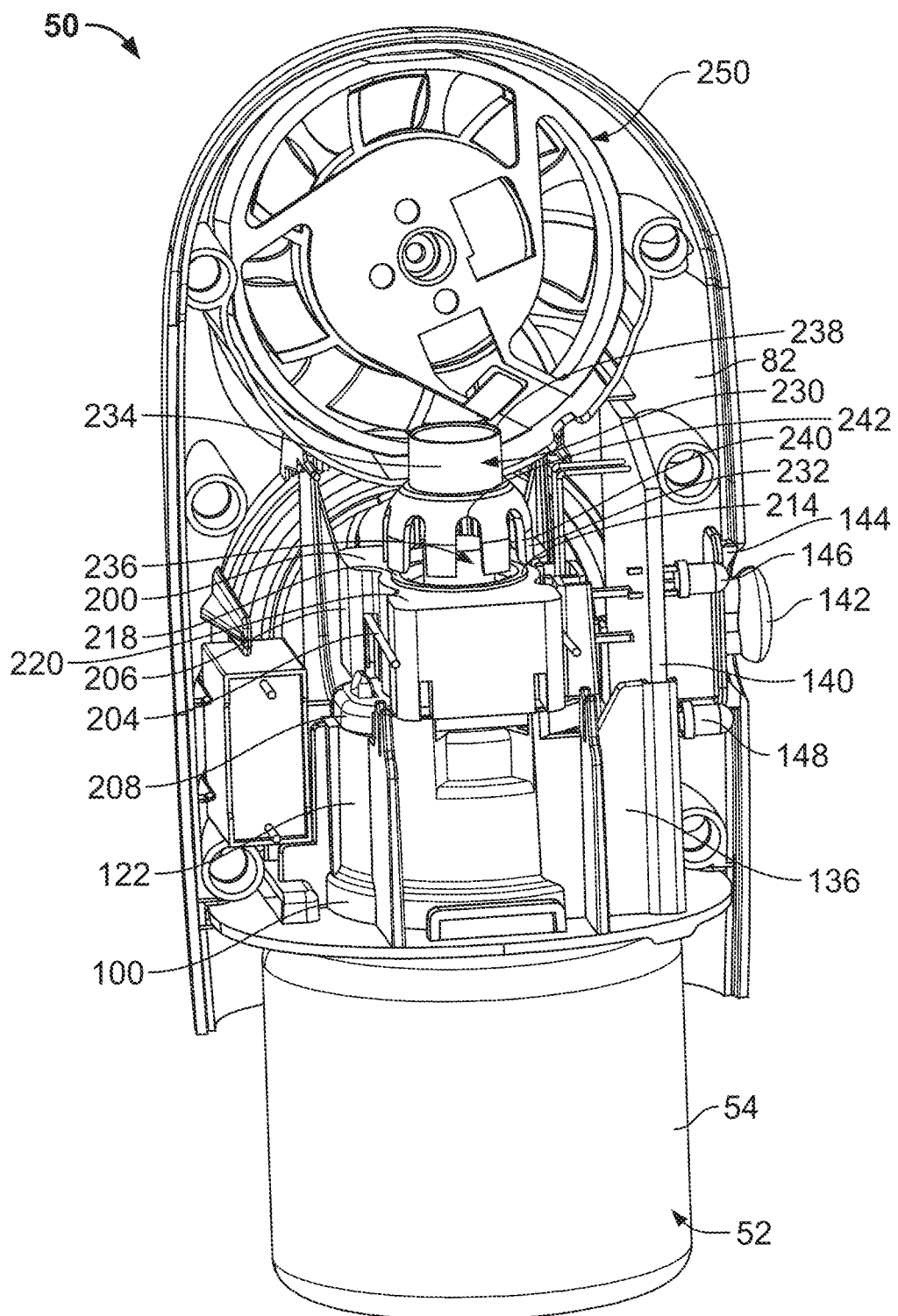
FIG. 11 is a front and top isometric view of another aspect of a dispensing system with a front portion of the housing removed to detail internal components of the dispensing system.
Figure 12:
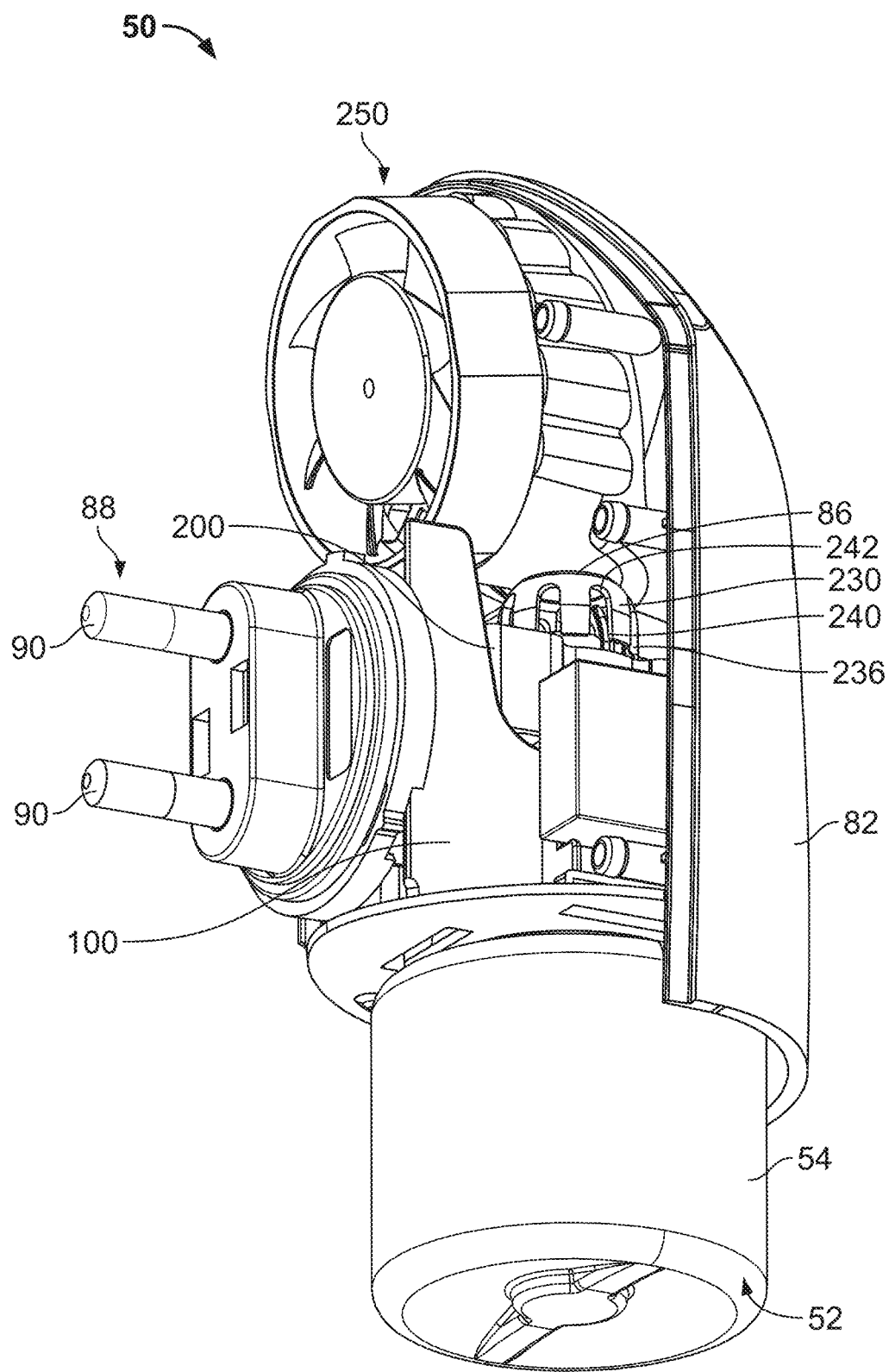
FIG. 12 is a side and bottom isometric view of the dispensing system of FIG. 10 with a rear portion of the housing removed to detail internal components of the dispensing system.

Turning now to FIGS. 10 and 11, in another aspect, rather than the dispenser 50 remaining substantially unobstructed between an upper, interior surface of the front portion 80 and an upper surface of the housing 206 of the heater arrangement 200, the dispenser 50 may include a separate chimney 230 configured to generally enclose the space between the upper surface 206 of the housing and the aperture 86. The chimney 230 may include a base portion 232 having a diameter or perimeter at least as large as the diameter or perimeter of the housing opening 210 or the conducting member 214. The base portion 232 may transition moving upwardly to a smaller diameter distal portion 234 having a diameter or perimeter sized to be received within the aperture 86.

The chimney 230 may define one or more openings 236 spaced around a periphery of the base portion 232. Preferably, a plurality of openings 236 is provided through the base portion 232. In a particular embodiment, the openings 236 are symmetrically spaced around the periphery of the base portion 232. An exit opening 238 is disposed at a top of the chimney 230. The openings 236 may serve to draw in air from the remainder of the first chamber 84, which is then heated by the heater assembly before leaving the chamber through the exit opening 238. The narrowing shape of the chimney 230, i.e., the decrease in diameter from the base portion 232 to the distal portion 234, may result in a decrease in volume in the chimney when moving upwards. As a result, air leaving via the exit opening 238 may be moving at a higher velocity than air entering through a sum of the openings 236 in the base portion 232, which may lead to better dispersal and a decrease in condensation of the volatilized material on the dispenser 50.

Each opening 236 may be similarly shaped as compared to the other openings. For example, the openings 236 may include a pair of generally parallel or converging sidewalls 240 joined by an arch-shaped wall 242 at the top of opening 236. Other shapes for the openings 236 are possible, as would be understood by one of ordinary skill in the relevant art.

Turning again to FIGS. 1-7, the dispenser 50 also includes a fan arrangement 250 to disperse the volatilized material into the surrounding environment. The fan arrangement 250 includes a fan 252 disposed in an upper portion of the housing 56, wherein the fan 252 has a plurality of blades 254 that rotate about a fixed axis $a_f$. The fan axis, $a_f$, may be inclined relative to a plane perpendicular to the wick and/or the aperture 86 by an amount, θ, e.g., between about 5 degrees and about 45 degrees in one aspect and between about 5 degrees and about 30 degrees in another aspect.

In one aspect, the fan may be rated at about 12 VDC and about 0.72 W, with a rated speed of 3000 RPM+/−about 20%, to produce an air output of between about 1.56 and about 1.95 CFM in free air. Other types of fans may be employed, however, as would be appreciated by one of ordinary skill in the relevant art. Additionally, FIGS. 11 and 12 illustrate that the dispenser 50 may include a capacitor 155, such as a 100 μF/50V capacitor, electrically coupled to at least the circuit board 140 and the fan 252 in order to provide a more predictable voltage to the fan 252 and to increase and stabilize the fan speed, e.g., at the rated speed of about 3000 RPM. Dispersion and reduced condensation of the volatilized material may benefit from this increased and stable fan speed.

When the dispenser 50 includes a second heater 202', the capacitor 155 may be in series with that heater 202', and both elements may be coupled in parallel with the first heater 202. Thus, the capacitor 155 may only be energized when the second heater 202' is activated. This configuration may be particularly suitable when the fan 252 is not engaged when only the first heater 202 is active, but instead is turned on in conjunction with energizing the second heater 202'.

The fan arrangement 250 includes a plurality of intake openings 256 disposed on the rear portion 82 of the housing 56 in order to draw air into the fan 252 and a plurality of output openings 258 disposed on the front portion 80 of the housing 56 in order to expel air from the fan arrangement 250, across the path of the volatized material exiting the aperture 86.

In one aspect, the intake openings 256 may be equally circumferentially and/or radially spaced about the fan axis, as best seen in FIG. 5. The plurality of intake openings may extend less than a full circumference about the fan axis, e.g., extending through about 270° of a circumference, with no openings at the bottom of the arc formed by the openings 256. Additionally, each intake opening 256 may be substantially similarly shaped in comparison to the other openings 256, with radially inward portions 260 of each opening being narrower than corresponding radially outward portions 262. While each intake opening 256 may be substantially similarly shaped, the openings may not be substantially similarly sized. For example, FIG. 5 depicts one aspect in which the lowermost openings **256*a* have a substantially uniform cross-section along their depths as the openings 256 but, at the same time, are smaller than the other intake openings 256. In one aspect, openings 256*a* may have a cross-sectional area between about 50% and about 90% of that of the openings 256. In another aspect, openings 256*a* may be between about 50% and about 75% of the cross-sectional size of the openings 256. In still another aspect, the openings 256*a* may be between about 75% and about 90% of the cross-sectional size of the openings 256. In still another aspect, the number, size, and/or layout of the intake openings 256 may be varied, e.g., to modify the ultimate airflow characteristics of the dispenser 50 or to provide additional cooling to the fan 252**.

Similarly, the output openings 258 also may be equally circumferentially and/or radially spaced about the fan axis. The output openings 258 may be disposed in a concave portion 264 of front portion 80, with radially inward portions 266 of each opening being narrower than corresponding radially outward portions 268. The output openings 258 may be circumferentially spaced about the fan axis at substantially equidistant intervals, although there may be a gap in that spacing. For example, the output openings 258 may form an arc extending through about 270° of a circumference, with no output openings 258 at a bottom of the arc. The concave portion 264 may define a solid panel 269 having a lack of output openings at the bottom of the arc formed by the openings 258, the solid panel 269 having a width substantially equal to a width of the aperture 86. The concave portion 264 may further define one or more secondary openings 276 within the gap, as discussed in greater detail below. Additionally, the concave portion 264 may include a leading edge 270 angled rearwardly from a front of the housing to a top of the housing, such that the aperture 86 is disposed laterally a greater distance away from the leading edge than the output openings 258.

At the same time, as seen in FIG. 2, the aperture 86 may elevated relative to the portions of the concave portion 264 disposed between the aperture 86 and the front of the dispenser 50. The aperture 86 may be disposed within a mounded section that falls off when moving forward. In one aspect, the upper end of the aperture 86 may be between about 5 mm and about 20 mm higher than the forwardmost portion of the concave portion 264 and, in another aspect, between about 5 mm and about 15 mm higher.

As seen by comparing FIGS. 1 and 5, the radially inward portions 266 of the output openings 258 may be disposed closer to the fan axis than the radially inward portions 260 of the intake openings 256, and the output openings 258 may be more numerous than the intake openings 256. Moreover, the output openings 258 may have a front-to-back depth significantly greater than a depth of the intake openings 256, e.g., between about 5 and about 10 times deeper than the intake openings 256. Additionally, the output openings 258 themselves may vary in depth, with output openings closer to the aperture 86 being the deepest (with the exception of secondary openings, as discussed below), and the remaining openings getting progressively shallower when moving upward.

Figure 4:
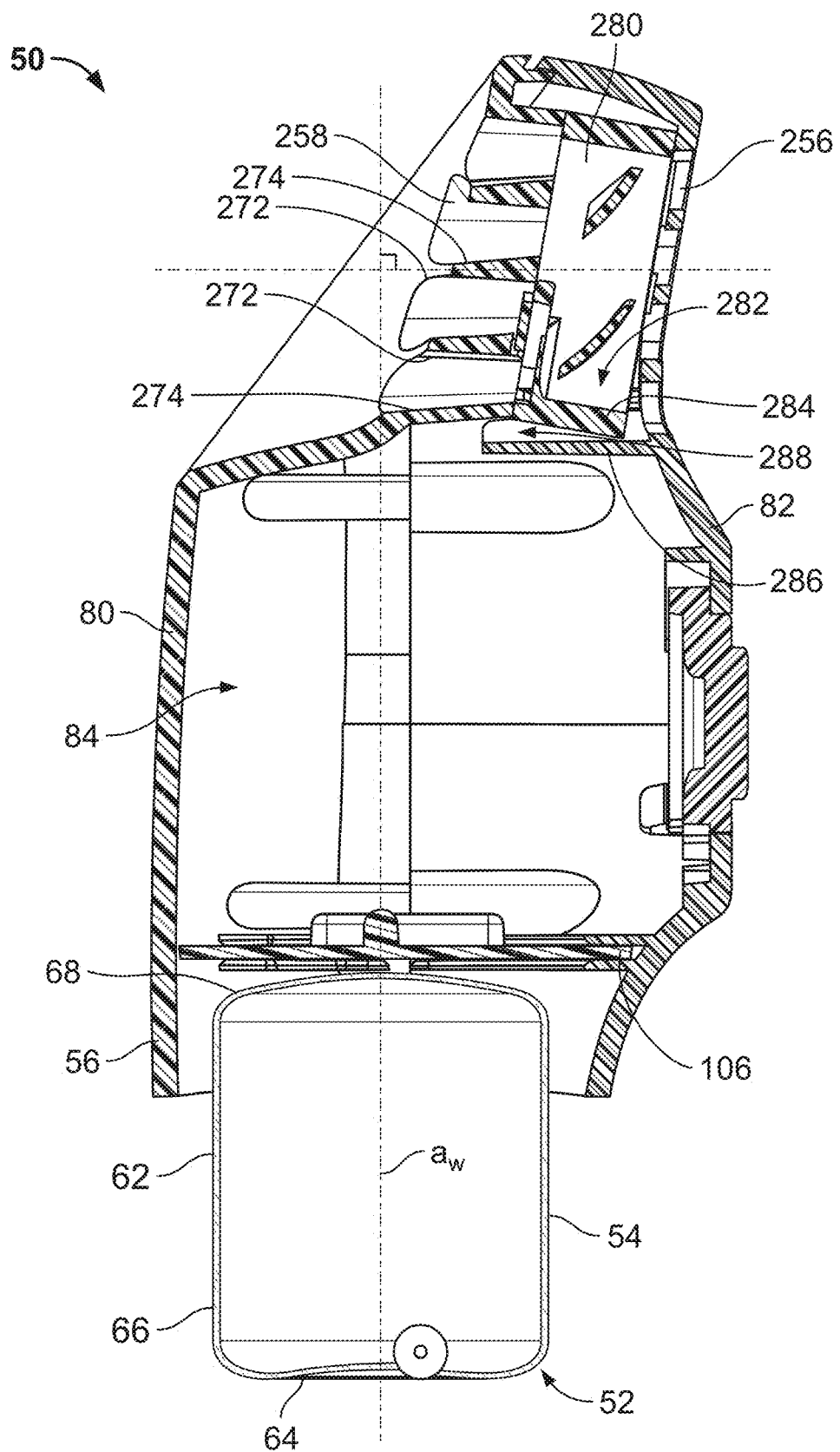
FIG. 4 is a cross-sectional view of the dispensing system taken generally along the line 4-4 of FIG. 1.

One or more output openings 258 may include an upper surface 272 angled upwardly relative to a line perpendicular to the wick 60, as best seen in FIG. 4. Conversely, one or more output openings 258 also may include a lower surface 274 angled downwardly relative to the line perpendicular to the wick 60.

As best seen in FIGS. 1 and 3, and as mentioned above, the dispenser 50 also may include one or more secondary output openings 276. The secondary openings 276 may be generally circumferentially aligned with the other output openings 258. At the same time, the secondary openings 276 may have significantly smaller cross-sections than the other output openings 258 and also may have significantly smaller front-to-back depths than the other output openings 258. For example, the secondary openings 276 may be approximately as deep as the intake openings 256, while having a cross-sectional area between about 10% and about 50% that of the other output openings 258. In another aspect, a cross-sectional area of the secondary openings 276 may be between about 10% and about 33% of a cross-sectional area of the other output openings 258, and in still another aspect, a cross-sectional area of the secondary openings 276 may be about 25% of a cross-sectional area of the other output openings 258. Thus, due to the smaller cross-section and shorter depth, airflow through the secondary openings 276 may be more restricted as compared to through the remainder of the output openings 258.

Whereas the output openings 258 may have lower surfaces 274 angled downwardly, the secondary output openings 276 may be oriented such that their internal surfaces are perpendicular to the wick axis, $a_w$, and/or to the outer surface of the aperture 86. This orientation may assist in preventing airflow from the fan from coming in direct contact with the aperture 86, thereby maintaining an elevated temperature of the volatilized material at and around the aperture 86 and, as a result, minimizing condensation of that material in the area proximate the aperture 86.

An equal or unequal number of secondary openings 276 may be disposed on opposite sides of the aperture 86 when the dispenser is viewed from the front, and the openings 276 may be oriented to direct airflow away from the aperture 86. As seen in FIG. 2, the secondary openings 276 also may be aligned with a rearward edge of the aperture 86, i.e., radially spaced from the axis, $a_w$, substantially the same distance. Put another way, a forwardmost portion of the secondary openings 276 is substantially the same distance from a front of the dispenser 50 as a rearwardmost portion of the aperture 86. To further assist in dispersal of the volatilized material, the output openings 258 and/or the secondary output openings 276 may be disposed radially away from the fan axis $a_f$ so as to receive maximum airflow from the fan blades 254. In the example shown in FIGS. 1-4, this may involve positioning the output openings 258 and/or the secondary output openings 276 radially inward from distal ends 278 of the fan blades. Any one or more of these features may yield a more efficient vapor plume, promoting dispersal of the volatilized material into the environment and reducing condensation of the material back onto the dispenser 50.

In order to further inhibit airflow from the fan arrangement 250 from acting on the volatilized material until that material has exited the aperture 86, the fan arrangement 250 may be disposed in a second cavity 280 separate and isolated from the cavity 84. As such, the dispenser 50 may include a thermal and/or airflow barrier 282 to keep heat within the cavity 84 and to minimize the effects in the cavity 84 of cooling caused by the fan 252, as seen in FIGS. 2-4. The thermal barrier 282 may include a first wall 284 completely separating the cavity 84 from the second cavity 280. The thermal barrier 282 also may include a second wall 286 at least partially separating the cavity 84 from the second cavity 280, the two walls forming an air gap 288 between the two cavities.

Turning to FIG. 13, a gas temperature plot taken along a centerline plane of a dispenser 50 incorporating a 4 W fan operating at about 25% capacity or about 3000 rpm is provided. At that setting, the fan may produce approximately 0.45 cfm of air flow, although it will be appreciated that larger or smaller air flows may be achieved by varying the size of the fan or the rotational speed of the fan. As this figure illustrates, the plume of volatilized material exits the first chamber 84 at the aperture 86 at an elevated temperature of almost 29° C. and hugs the housing 56 until it passes in front of the openings 258. That elevated temperature remains substantially constant along all but the uppermost opening 258, maintaining the material in a volatilized state. Due to the geometry and subsequent airflow through the openings 258, the volatilized material is then dispersed up and away from the housing 56 in a direction generally parallel to the inclined fan axis, $a_f$, to be dispersed into the surrounding environment.

Figure 9:
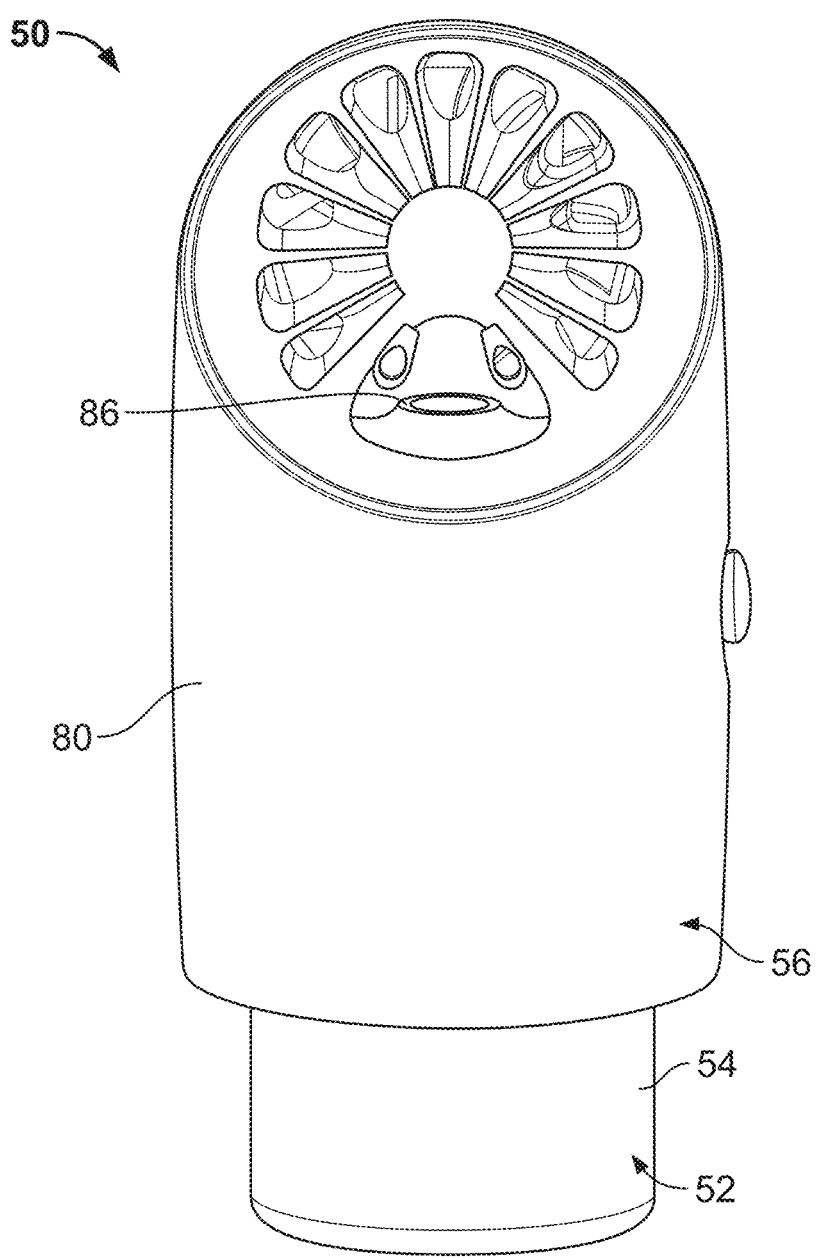
FIG. 9 is a front view of the dispensing system of FIG. 1.

FIG. 13 also illustrates that air temperatures within the fan arrangement 250 are significantly cooler than the temperatures both of the volatilized material that has exited the first chamber 84 and within that chamber 84 itself. In particular, air temperatures within the fan arrangement 250 may be approximately 2° C. lower than those other elevated temperatures. Still further, FIG. 9 illustrates the effect of the first wall 284 and/or the second wall 286 within the thermal barrier 282 as it relates to insulation between the first chamber 84 and the fan arrangement 250. In particular, the temperature plot indicates a substantially uniform elevated temperature in the first chamber 84 in the vicinity of the thermal barrier 282 and a substantially uniform reduced temperature in the fan arrangement 250 in the vicinity of the thermal barrier 282 without any (or substantially any) leakage from one section to the other. As such, the thermal barrier 282 serves to substantially eliminate thermal transfer between the first chamber 84 and the fan arrangement 250.

Figure 14:
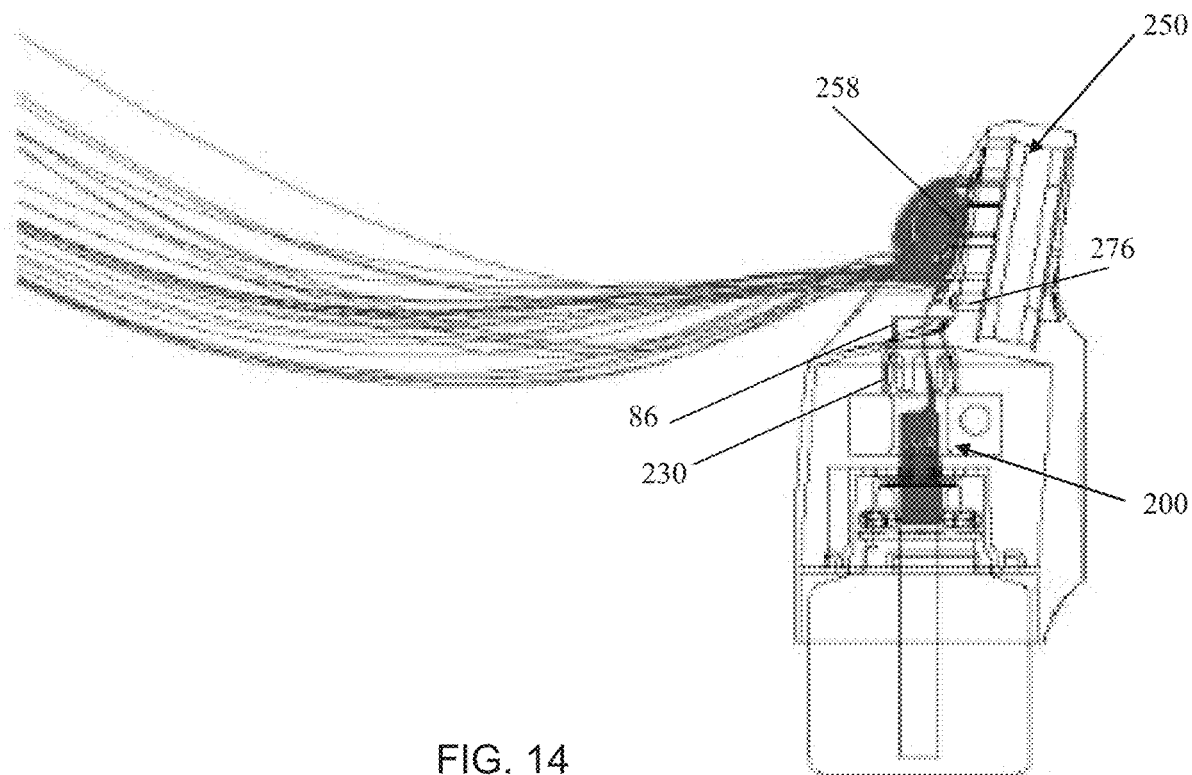
FIG. 14 is a pathline plot depicting the movement of the volatilized material only of the dispensing system of FIGS. 10 and 11 taken generally along the line 13-13 of FIG. 10.
Figure 15:
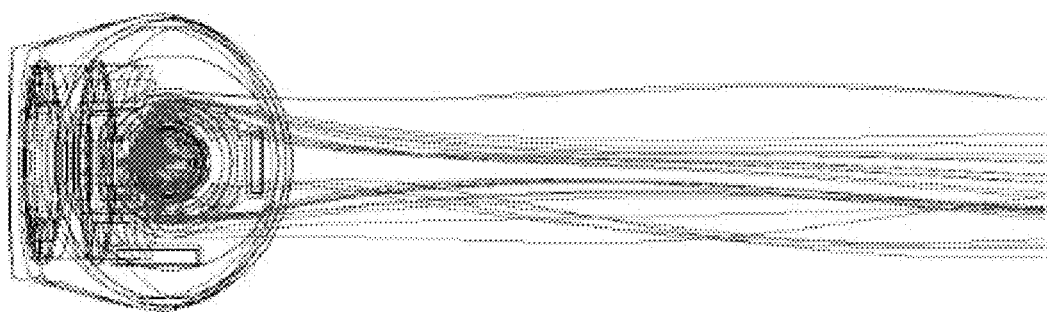
FIG. 15 is a top view pathline plot depicting the movement of the volatilized material only of the dispensing system of FIGS. 10 and 11.
Figure 16:
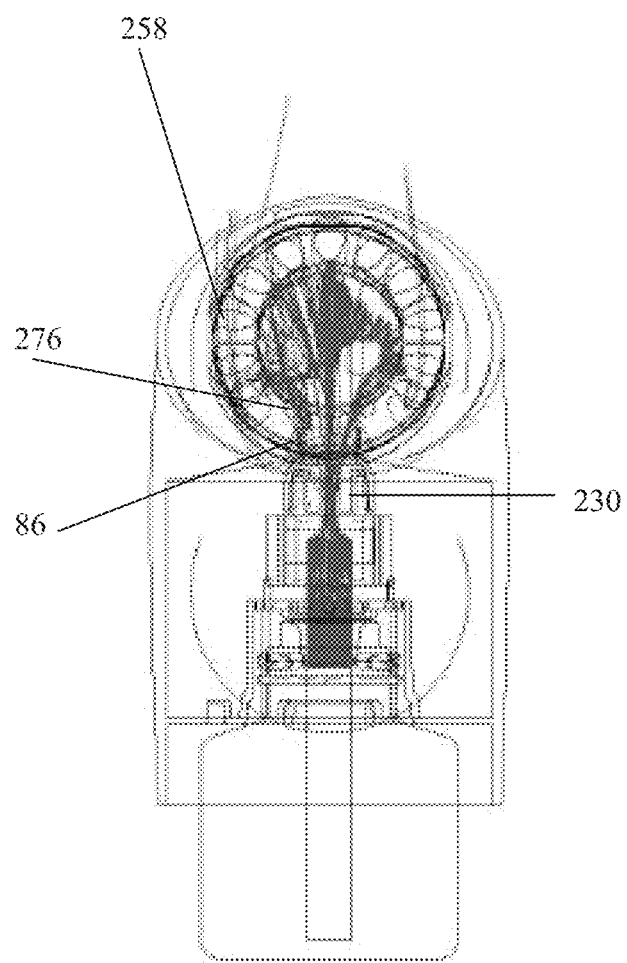
FIG. 16 is a pathline plot depicting the movement of the volatilized material only of the dispensing system of FIGS. 10 and 11 taken generally perpendicular to the line 13-13 of FIG. 10.

Turning now to FIGS. 14-16, pathlines depicting a 3-D dispersal pattern of the volatilized material are shown. From those images, it again can be seen that the plume of volatilized material disperses upward, hugging the front portion 80 of the housing 56. The plume dips slightly, but not far enough to condense on the aperture 86 or other portions of the housing, before dispersing outward and into the environment. Additionally, by the time the plume has dipped to a height where it can contact a portion of the housing 56, it already has dispersed outwardly, i.e., forwardly, enough to be past the housing 56, again inhibiting condensation of the plume on the housing 56. It also can be seen, particularly when viewed from above and in front, that the plume is focused and is substantially contained to a width equal to that of the dispenser refill 52.

Figure 17:
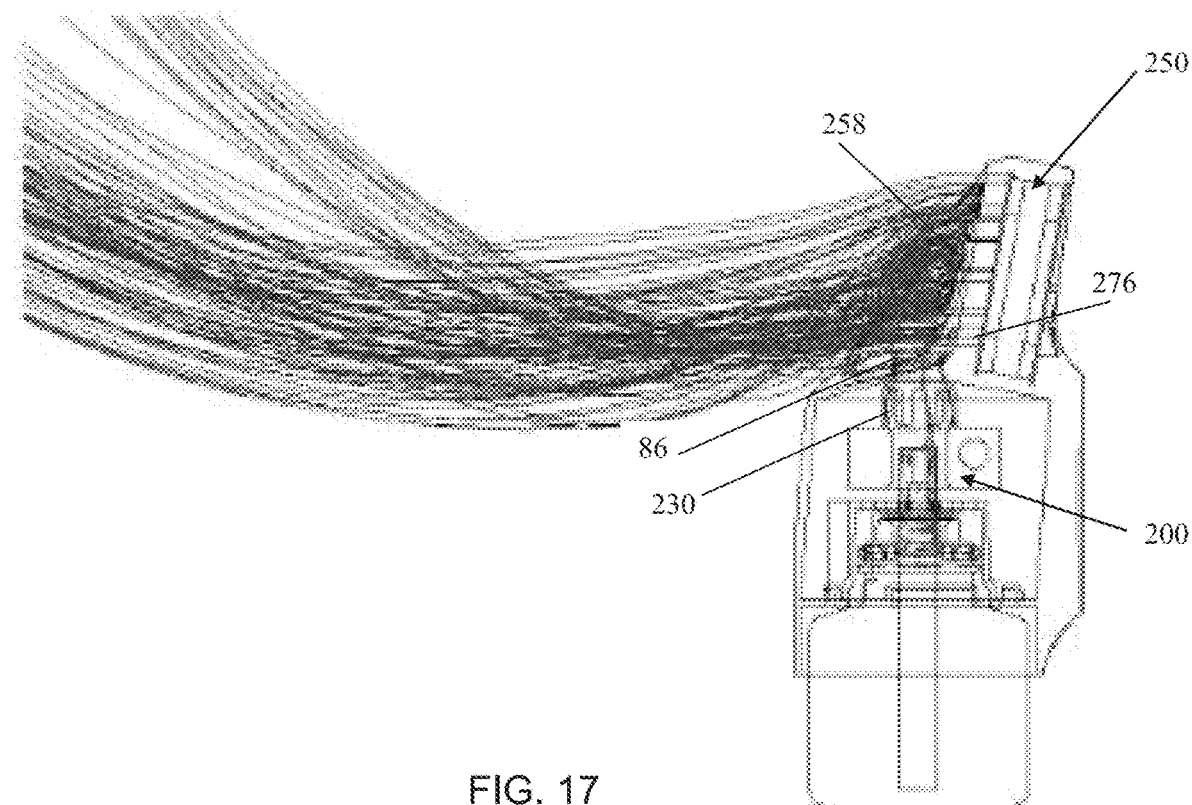
FIG. 17 is an airflow pathline plot depicting the movement of both the volatilized material and air expelled by the fan of the dispensing system of FIGS. 10 and 11 taken generally along the line 13-13 of FIG. 10.
Figure 18:
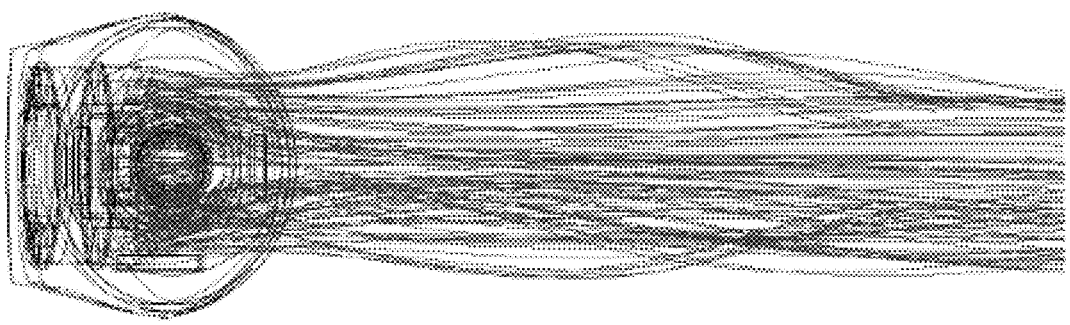
FIG. 18 is a top view air flow pathline plot depicting the movement of both the volatilized material and air expelled by the fan of the dispensing system of FIGS. 10 and 11 and FIG. 19 is an air flow pathline plot depicting the movement of both the volatilized material and air expelled by the fan of the dispensing system of FIGS. 10 and 11 taken generally perpendicular to the line 13-13 of FIG. 10.
Figure 19:
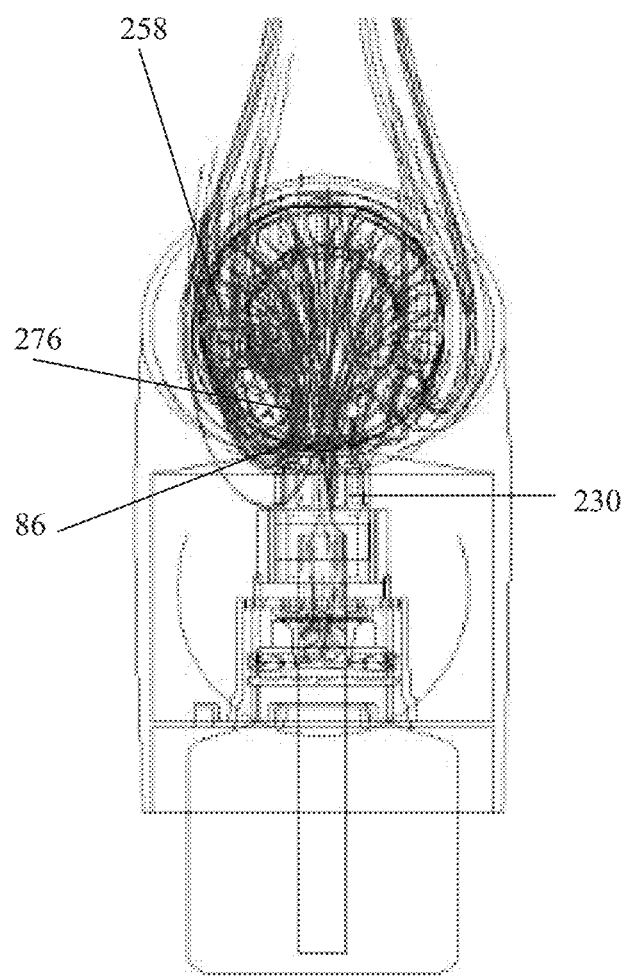

Similarly, FIGS. 17-19 illustrate pathlines depicting a 3-D dispersal pattern of the volatilized material when the fan 252 is on. The pathlines illustrate that, due to the geometry of the dispenser 50 as discussed above, rotational energy of air flow created by the fan 252 is reduced, thereby reducing radial dispersion of the volatilized material, increasing linear velocity, and increasing a distance of dispersion into the surrounding environment. FIGS. 18 and 19, in particular, illustrate that the volatilized material may be dispersed straight ahead, with minimal dispersal to either side of the dispenser 50.

Specifically, one or more of the larger output openings 258, the smaller secondary output openings 276, and the solid panel 269 may reduce airflow proximate the aperture and cause a higher airflow farther from the aperture 86. One or more of the shape of the upper and/or lower surfaces 272, 274 of the output openings 258 and the angling of the fan 252 may be responsible for directing the volatilized material upward and away from the aperture 86. Further, the shape of the elongated output openings 258 also may diminish the rotational energy of the fan, resulting in unidirectional airflow.

FIGS. 17 and 18 additionally illustrate the effect that the secondary output openings 276 may have on dispersal of the fan air and the vapor plume. In particular, these figures show that the airflow from those openings is directed generally horizontally away from the dispenser 50 and then upwardly into the environment more quickly than the rest of the airflow from the other output openings 258 is. Thus, volatilized material that comes into contact with air emitted by the secondary output openings 276 is quickly emitted into the environment. Similarly, volatilized material that makes it past those secondary output openings 276 and that sinks back down due to cooling has a second chance to come into contact with air emitted by the secondary openings 258. Thus, the present configuration quickly and efficiently disperses the volatilized material, thereby reducing condensation of that material on the dispenser.

One skilled in the art should understand that variations of the heater and fan arrangements as disclosed herein may be utilized. For example, any number of the features of any of the embodiments herein may be combined to further increase heater efficiency, decrease overall power consumption, and minimize condensation in the vicinity of the dispenser 50.

Any of the embodiments described herein may be modified to include any of the structures or methodologies disclosed in connection with other embodiments.

Further, although directional terminology, such as front, back, top, bottom, upper, lower, etc., may be used throughout the present specification, it should be understood that such terms are not limiting and are only utilized herein to convey the orientation of different elements with respect to one another.

Any of the embodiments described herein may be modified to include any of the structures or methodologies disclosed in connection with different embodiments. Further, the present disclosure is not limited to the heater mechanism, the fan arrangement, and/or the dispensing device of the type specifically shown. Still further, the support for any component of any of the embodiments disclosed herein may be chosen or modified to work with various types of volatiles consistent with the disclosure herein.

INDUSTRIAL APPLICABILITY

Dispensers are commonly used to dispense a variety of volatile materials such as air fresheners, deodorants, insecticides, germicides, perfumes, and the like, that are stored within refill containers. Heating and fan components allow the volatile materials to be volatilized and then distributed into an environment in order for the contents thereof to be released without human interaction, for example, continuously or according to a predetermined time schedule.

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved. Additionally, each of the references cited herein, including U.S. Pat. No. 7,032,831, U.S. Patent Publication 2014/0037273, and U.S. Patent Publication 2011/0139885, are incorporated herein by reference in their entirety.

We claim:

1. A volatile material dispenser, comprising:
   a housing configured to receive a refill containing a volatile material and a wick, the housing including a first cavity supporting a heater and a second, separate cavity supporting a fan for dispersing a vapor plume of the volatile material, and
   a chimney between an upper, interior surface of the housing and an upper surface of the heater,
   wherein the housing includes an aperture through which the vapor plume exits the housing,
   wherein the housing includes a plurality of openings through which air from the fan is directed across the vapor plume, the aperture being located in the housing to be laterally within an arc defined by the plurality of openings, and
   wherein the dispenser is configured such that, when the refill is received within the housing, the upper surface of the heater is disposed nearer the aperture than a distal end of the wick and a radial gap is formed between the heater and the wick.

2. The volatile material dispenser of claim 1, wherein the heater includes a positive temperature coefficient (PTC) heating element configured to provide radiant heating around a plurality of sides of the wick.

3. The volatile material dispenser of claim 1, further comprising a thermal barrier between the first cavity and the second cavity.

4. The volatile material dispenser of claim 3, wherein the thermal barrier comprises at least one wall fluidly isolating the first cavity from the second cavity.

5. The volatile material dispenser of claim 4, wherein the thermal barrier comprises a second wall overshadowing the first wall.

6. The volatile material dispenser of claim 1, wherein the plurality of openings includes primary openings and at least one secondary opening, wherein the at least one secondary opening is sized differently than each of the primary openings.

7. The volatile material dispenser of claim 6, wherein:
   each of the primary openings is defined in a wall of the housing and has a primary front-to-back depth through the wall, the at least one secondary opening is defined in the wall and has a secondary front-to-back depth through the wall, and the secondary front-to-back depth is shorter than each of the primary front-to-back depths.

8. The volatile material dispenser of claim 6, wherein the at least one secondary opening includes a pair of openings disposed on opposite sides of the aperture.

9. The volatile material dispenser of claim 6, wherein the fan includes a plurality of blades that rotate about a fan axis, wherein a maximum airflow occurs along the plurality of blades at a first radial distance from the fan axis, and wherein the at least one secondary opening is radially spaced from the fan axis by the first radial distance.

10. The volatile material dispenser of claim 1, wherein the aperture is vertically aligned with the wick.

11. A volatile material dispenser, comprising:

a housing configured to receive a refill containing a volatile material and a wick, the housing supporting a heater to volatize the volatile material into a vapor plume, the housing further supporting a fan for dispersing the vapor plume, wherein the housing includes an aperture extending along a first axis and through which a vapor plume of the volatized material exits the housing, wherein the housing includes a plurality of openings through which air from the fan is directed across the vapor plume, the aperture being located in the housing to be laterally within an arc defined by the plurality of openings, wherein at least one of the fan and the plurality of openings is angled along a second axis, the second axis angled upward relative to a line perpendicular to the first axis, wherein the plurality of openings includes primary openings and secondary openings, the secondary openings disposed closest to the aperture, wherein each of the primary openings has a lower surface sloping downwardly from the fan toward the aperture, and wherein each of the secondary openings has a lower surface perpendicular to the first axis.

12. The volatile material dispenser of claim 11, wherein:

each of the primary openings is defined in a wall of the housing and has a primary front-to-back depth through the wall, each of the secondary openings is defined in the wall and has a secondary front-to-back depth through the wall, and each of the secondary front-to-back depths is shorter than each of the primary front-to-back depths.

13. The volatile material dispenser of claim 12, wherein the fan includes a plurality of blades that rotate about a fan axis, the plurality of blades defining a blade diameter, and wherein at least some of the plurality of secondary openings are spaced radially from the fan axis to be within the blade diameter.

14. The volatile material dispenser of claim 12, wherein ones of the primary openings closer to a top of the housing are shallower than ones of the primary openings closer to the aperture.

15. The volatile material dispenser of claim 11, wherein the heater is substantially aligned with a distal end of the wick.

16. The volatile material dispenser of claim 11, wherein the heater includes a positive temperature coefficient (PTC) heating element configured to provide radiant heating around a plurality of sides of the wick.

17. The volatile material dispenser of claim 11, further comprising at least one wall completely separating the heater from the fan.

18. The volatile material dispenser of claim 17, further comprising at least one secondary wall partially separating the heater from the fan.

19. A volatile material dispenser, comprising:

a housing configured to receive a refill containing a volatile material and a wick, the housing supporting a heater to volatize the volatile material into a vapor plume, the housing further supporting a fan for dispersing the vapor plume, wherein the housing includes a concave upper surface defining an aperture through which a vapor plume of the volatized material exits the housing and a plurality of openings through which air from the fan is directed across the vapor plume, the aperture being located in the housing to be laterally within an arc defined by the plurality of openings, wherein the concave upper surface includes a leading edge angled rearwardly from a front of the housing to a top of the housing, such that ones of the plurality of openings closer to the aperture are deeper than ones of the plurality of openings closer to the top of the housing, and wherein the aperture is elevated relative to a portion of the concave upper surface disposed between the aperture and a front of the housing, the portion of the concave upper surface sloping downwardly from the aperture toward the front.

20. The volatile material dispenser of claim 19, wherein the fan includes a plurality of blades that rotate about a fan axis, the plurality of blades defining a blade diameter, wherein the plurality of openings includes a pair of openings disposed closest to the aperture, and wherein the pair of openings are spaced radially from the fan axis to be within the blade diameter.

* * * * *